United States Patent
Zlotnick et al.

(10) Patent No.: US 10,607,122 B2
(45) Date of Patent: Mar. 31, 2020

(54) SYSTEMS AND USER INTERFACES FOR ENHANCEMENT OF DATA UTILIZED IN MACHINE-LEARNING BASED MEDICAL IMAGE REVIEW

(71) Applicant: International Business Machines Corporation, Armonk, NY (US)

(72) Inventors: Aviad Zlotnick, Mitzpeh Netifah (IL); Alon Hazan, Zikhron Ya'akov (IL); Murray A. Reicher, Rancho Santa Fe, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 168 days.

(21) Appl. No.: 15/831,057

(22) Filed: Dec. 4, 2017

(65) Prior Publication Data
US 2019/0171914 A1    Jun. 6, 2019

(51) Int. Cl.
*G06K 9/66* (2006.01)
*G06K 9/62* (2006.01)
*G06F 3/0484* (2013.01)

(52) U.S. Cl.
CPC ........... *G06K 9/66* (2013.01); *G06F 3/04845* (2013.01); *G06K 9/6254* (2013.01); *G06K 9/6263* (2013.01); *G06K 9/6267* (2013.01); *G06K 2209/05* (2013.01)

(58) Field of Classification Search
CPC ..... G06K 9/66; G06K 9/6267; G06F 3/04845
See application file for complete search history.

(56) References Cited

U.S. PATENT DOCUMENTS 8,520,017 B2 * 8/2013 Kondo .................. G06F 19/321
345/530
9,247,145 B2 * 1/2016 Nihei ................. H04N 1/00442
(Continued)

FOREIGN PATENT DOCUMENTS

WO    WO 2013/019856 A1    2/2013

OTHER PUBLICATIONS

Holmes et al. "An Interactive Java Statistical Image Segmentation System: GemIdent", Journal of Statistical Software, Jun. 1, 2009 pp. 1-22, https://www.ncbi.nlm.nih.gov/pmc/articles/PMC3100170/. (Year: 2009).*

*Primary Examiner* — Brenda C Bernardi
(74) *Attorney, Agent, or Firm* — Michael Best & Friedrich LLP

(57) ABSTRACT

Systems and techniques are disclosed for improvement of machine learning systems based on enhanced training data. An example method includes generating an interactive classification user interface concurrently displaying a first group of medical images and a second group of medical images, each group depicting objects associated with a respective classification. User input indicating movement of medical images from the first group to the second group is detected. The moved medical images are classified according to the second group. The re-classified medical images are provided to a machine learning system, with the machine learning system updating based on analysis of object characteristics of the re-classified medical images to increase accuracies associated with automated assignment of classifications.

20 Claims, 14 Drawing Sheets

(56) References Cited

U.S. PATENT DOCUMENTS

| | | | |
|---|---|---|---|
| 2005/0105806 A1* | 5/2005 | Nagaoka | G06F 16/583 |
| | | | 382/224 |
| 2006/0192881 A1* | 8/2006 | Sato | G06F 3/04817 |
| | | | 348/333.05 |
| 2011/0182493 A1 | 7/2011 | Huber et al. | |
| 2013/0070986 A1 | 3/2013 | Peleg et al. | |
| 2013/0101199 A1* | 4/2013 | Alexandrov | G06K 9/0014 |
| | | | 382/133 |
| 2013/0129165 A1 | 5/2013 | Dekel et al. | |
| 2014/0118395 A1* | 5/2014 | Jirman | G06T 11/00 |
| | | | 345/629 |
| 2014/0257854 A1 | 9/2014 | Becker et al. | |
| 2014/0341476 A1* | 11/2014 | Kulick | G06K 9/6267 |
| | | | 382/224 |
| 2014/0348387 A1 | 11/2014 | Choi et al. | |
| 2015/0254555 A1 | 9/2015 | Williams, Jr. et al. | |
| 2016/0171682 A1 | 6/2016 | Abedini et al. | |
| 2016/0350919 A1 | 12/2016 | Steigauf et al. | |
| 2017/0098329 A1 | 4/2017 | Westerhoff et al. | |
| 2017/0200067 A1 | 7/2017 | Zhou et al. | |
| 2018/0137394 A1* | 5/2018 | Wenzel | G06T 7/0012 |
| 2019/0087944 A1* | 3/2019 | Chakraborty | B60K 35/00 |

* cited by examiner

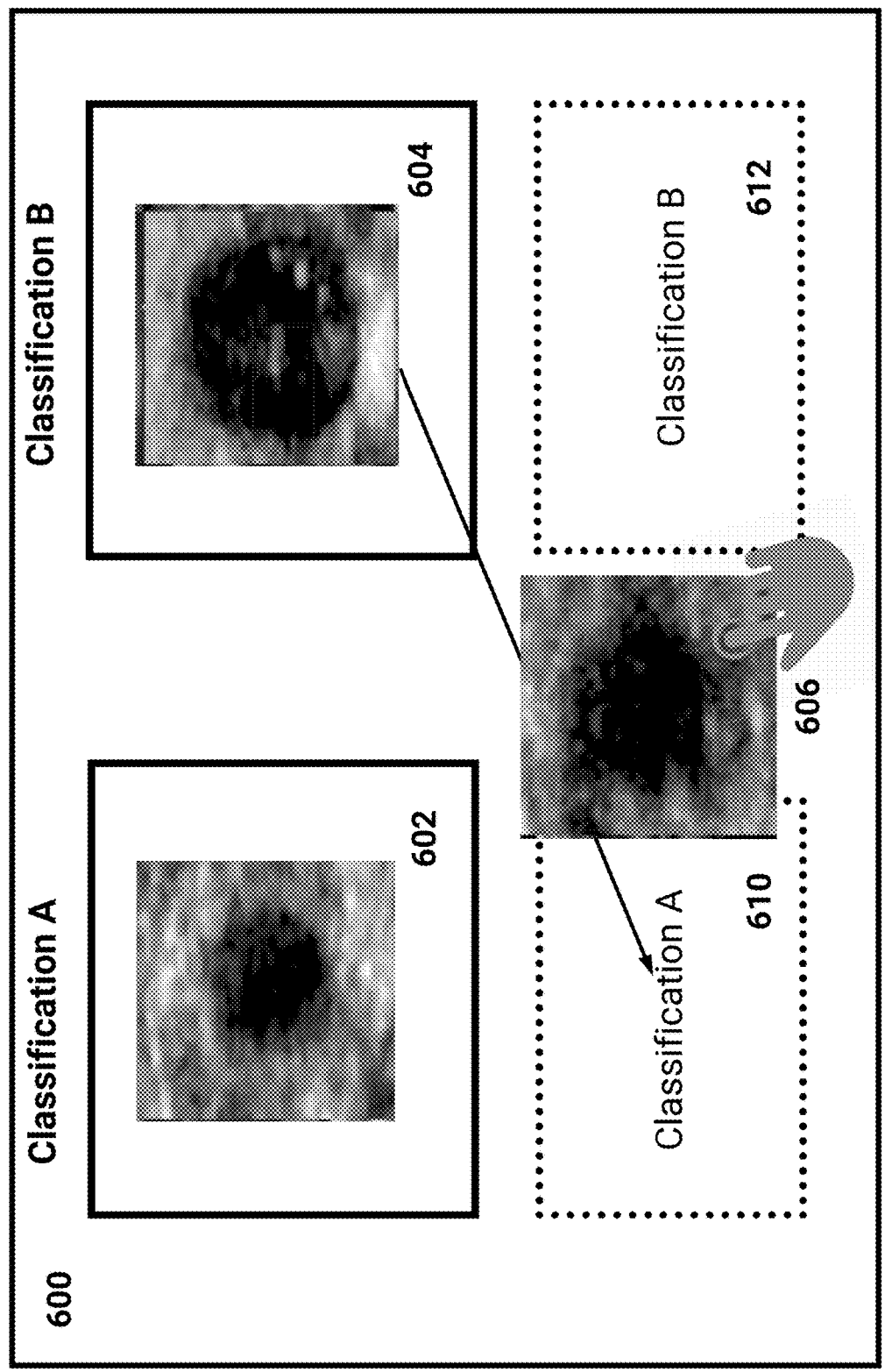

SYSTEMS AND USER INTERFACES FOR ENHANCEMENT OF DATA UTILIZED IN MACHINE-LEARNING BASED MEDICAL IMAGE REVIEW

TECHNICAL FIELD

Embodiments of the present disclosure relate to systems and techniques for improving machine learning models used in classification of objects in medical image data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Machine learning systems, such as neural network based systems, typically rely on training data to be effective. An example system that implements a neural network may ingest information indicating outcomes for particular inputs. This ingested information may be training data, and the neural network can be trained based on the information. Subsequent to training the neural network, the example system can receive real data and determine outputs associated with the real data. For example, a neural network can be trained to identify particular features in images. Other machine learning systems may utilize training data to generate a model enabling the systems to produce sufficiently accurate predictions in newly received data.

Obtaining such training data can present technical difficulties, and ensuring the accuracy of such training data can be difficult. For example, training a machine learning system to precisely label particular features can require training images with accurate feature labels. The accuracy of these feature labels can be dependent upon a reviewing user, or a system automatically generating labels, and therefore the accuracy of the machine learning system can be lower with lesser accurate training images.

SUMMARY

The systems, methods, and devices described herein each have several aspects, no single one of which is solely responsible for its desirable attributes. Without limiting the scope of this disclosure, several non-limiting features will now be described briefly.

Particular embodiments of the subject matter described in this specification can be implemented so as to realize one or more of the following advantages. A system can present medical images of patients and enable accurate classifications to be assigned to each medical image. These classified medical images can be provided to one or more machine learning systems, for example as ground-truth or training data. To enhance consistent classification, the system can present medical images as a montage, which as will be described is a collection of medical images concurrently presented. In this way, a reviewing user of the presented medical images can utilize contextual information presented in the montage to more consistently classify objects in the medical images.

As an example, particular example systems may present a first medical image, and a reviewing user can classify the first medical image or, more particularly, an object present in a portion of the medical image, such as a suspected lesion. For example, the first medical image may be an ultrasound of a breast with a lesion. In this example, the reviewing user may classify the lesion as being round or heterogeneous. A proper classification can inform whether the lesion is benign or malignant. For these example systems, the reviewing user can classify the first medical image in a complex user interface, for example viewing disparate views related to the first medical image and medical history of a patient, and then viewing a second medical image. The user may then move on to other medical images (e.g., of the same or different patients) and classify objects in those medical images. That is, the reviewing user can view individual medical images, and classify objects in the medical images individually, without the benefit of comparison to other objects with the same or similar classifications.

The above-described scheme of cycling through subsequent medical images may produce inconsistent classification results. For example, there may be mistakes in such a classifying process, as the reviewing user is unable to directly view multiple medical images and concurrently provide classifications of multiple medical images. Instead, the reviewing user is only able to view a single medical image and try to rely on a consistent classification being applied to each medical image. In this way, contextual information that may be evident between the medical images is lost, and for each freshly presented medical image, the reviewing user is less likely to maintain a consistent classification process, e.g., classifying an object with a particular border as round on one medical image and then later classifying an object with the same border as an oval on a later-viewed medical image. Such inconsistencies in object classification can not only impact diagnosis of the patient's involved, but reduce accuracy of machine learning that develops object classification models based on the (inconsistent) user-provided classifications.

As will be described below, a system can present a montage of medical images in a user interface. A reviewing user can view the montage, and classify multiple medical images in the user interface. Since the reviewing user can easily view the medical images side-by-side in the montage, the reviewing user can more readily ensure consistency between the classifications. In this way, accuracy of the classified medical images can be improved. Furthermore, since these classified medical images can be utilized by a machine learning system as training data, the accuracy of such machine learning systems can be improved.

Therefore, the subject matter described in this specification improves the functioning of the computer. Through the user interfaces described herein, a reviewing user can more accurately classify, characterize, and so on, medical images. These medical images can, as described above, improve the functioning of systems (e.g., computers) that implement machine learning. Additionally, the specific presentation of montages of medical images can be automatically customized by systems to further increase accuracy of classifications. For example, if the montage includes less than a threshold of a certain classification (e.g., round lesions), a system can update the montage to include additional medical images which can be classified. Optionally, these additional medical images may be control images known (e.g., as reviewed by one or more reviewing users or by automated systems) to be of the certain classification. The reviewing user can utilize these control images to ensure he/she is appropriately classifying the medical images. Optionally, the system can include the additional medical images based on a determination that the certain classification is underrepresented statistically. For example, the certain classification may be known apply to a particular percentage of medical images, and if the reviewing user classified less than the particular percentage (e.g., one or more standard deviations from the particular percentage), the additional images can be included. In this way, a reviewing user's deficiency, or apparent bias against, a particular classification can be determined.

Furthermore, the subject matter described in this specification solves problems arising out of use of technology. In addition to improving the functioning of computers (e.g., computers implementing machine learning techniques), the subject matter improves efficiencies associated with classifying images. For example, utilizing the user interfaces described herein, a reviewing user can more readily correctly classify medical images. Thus, through utilization of the user interfaces, an amount of time to correctly classify medical images can be reduced, which enables a greater efficiency in such classifications. With respect to the control images described above, a reviewing user's performance can be evaluated and utilized to determine whether to maintain, or discard, the reviewing user's classifications. For example, control images can be dynamically included in a montage, and whether the reviewing user correctly classifies these control images can be monitored. Optionally, multiple reviewing users can separately review medical images, and based on their performance with respect to classifying the control images, classifications assigned to each medical image can be weighted. For example, if a first reviewing user correctly classifies all control images, his/her classification of a particular medical image may be preferred over a second reviewing user who does not correctly classify all control images. In this way, the subject matter described herein can aggregate classifications via user interfaces, and thus cause more accurate classifications of medical images.

Embodiments of the present disclosure relate to systems and techniques for accessing data stores of medical images and displaying the medical images to efficiently provide information in an interactive user interface. Previous systems for display of, and interaction with, image data were typically inefficient at presenting medical information. For example, previous systems may provide singular medical images one at a time, resulting in less accurate classifications. Disclosed herein are systems that, according to various embodiments, advantageously provide highly efficient, intuitive, and rapid dynamic interaction with medical images (including two-dimensional images and images rendered from three-dimensional image data). The systems may include interactive user interfaces that are dynamically updated to enable rapid classifications of medical images.

Design of computer user interfaces "that are useable and easily learned by humans is a non-trivial problem for software developers." (Dillon, A. (2003) *User Interface Design*, MacMillan Encyclopedia of Cognitive Science, Vol. 4, London: MacMillan, 453-458.) The present disclosure describes various embodiments of interactive and dynamic user interfaces that are the result of significant development, including related development of deep-learning and artificial intelligence techniques for review of medical images. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface via the inputs described herein may provide an optimized display of, and interaction with, image data (including medical images) and may enable a user to more quickly and accurately access, navigate, assess, and digest the image data than previous systems.

Further, the interactive and dynamic user interfaces described herein are enabled by innovations in efficient interactions between the user interfaces and underlying systems and components. For example, disclosed herein are improved methods of receiving user inputs (including methods of interacting with, and selecting, images), translation and delivery of those inputs to various system components, automatic and dynamic execution of complex processes in response to the input delivery, automatic interaction among various components and processes of the system, and automatic and dynamic updating of the user interfaces (to, for example, display the relevant medical images). The interactions and presentation of data via the interactive user interfaces described herein may accordingly provide cognitive and ergonomic efficiencies and advantages over previous systems.

Various embodiments of the present disclosure provide improvements to various technologies and technological fields. For example, as described above, existing medical image interaction technology (including, e.g., Picture Archiving and Communication Systems, Electronic Medical Record Systems, and/or the like) is limited in various ways (e.g., image review is slow and cumbersome), and various embodiments of the disclosure provide significant improvements over such technology. Additionally, various embodiments of the present disclosure are inextricably tied to computer technology. In particular, various embodiments rely on detection of user inputs via graphical user interfaces, calculation of updates to displayed electronic data based on those user inputs, automatic processing of related electronic medical images, and presentation of the updates to displayed medical images via interactive graphical user interfaces. Such features are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic image data.

Additional embodiments of the disclosure are described below in reference to the appended claims, which may serve as an additional summary of the disclosure.

In various embodiments, computer-implemented methods are disclosed in which, under control of one or more hardware computing devices configured with specific computer executable instructions, one or more aspects of the above-described embodiments (including one or more aspects of the appended claims) are implemented and/or performed.

In various embodiments, non-transitory computer-readable storage mediums storing software instructions are disclosed, wherein, in response to execution by a computing system having one or more hardware processors, the software instructions configure the computing system to perform operations comprising one or more aspects of the above-described embodiments (including one or more aspects of the appended claims).

Further, as described herein, various embodiments of the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 6C illustrates another example user interface for re-classifying medical images.

Figure 1:
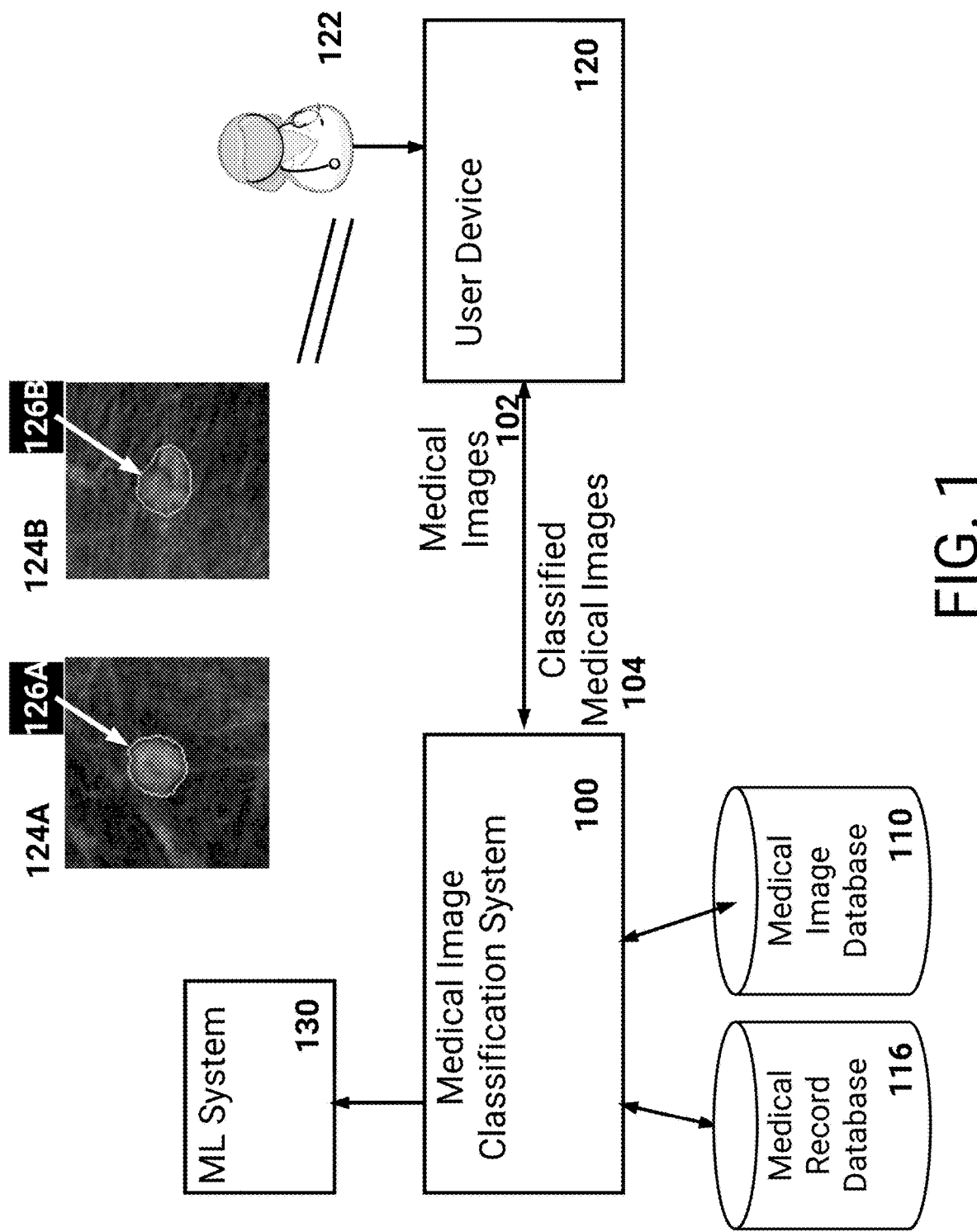
FIG. 1 illustrates an example of a medical image classification system.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

DETAILED DESCRIPTION

I. Definitions

In order to facilitate an understanding of the systems and methods discussed herein, a number of terms are defined below. The terms defined below, as well as other terms used herein, should be construed broadly to include the provided definitions, the ordinary and customary meaning of the terms, and/or any other implied meaning for the respective terms. Thus, the definitions below do not limit the meaning of these terms, but only provide exemplary definitions.

User: Also referred to herein as "reviewer" and/or "viewer." An individual (or group of individuals) that interfaces with a computing device to, for example, view medical images. Users may include, for example, physicians (including, for example, doctors, radiologists, etc.) hospital staff, and/or any other individuals (including persons not medically trained) involved in analysis, annotation, comparison, acquisition, storage, management, or other tasks related to medical images (or any other types of images) as described herein. Any discussion herein of user preferences and/or rules associated with users should be construed to also, or alternatively, include user group preferences (or rules associated with groups of users), site preferences/rules, system preference/rules, and/or default software preferences/rules.

Medical Image (also referred to herein as an "Image"): Any type of image of an organism (e.g., a human patient). It may include but is not limited to a radiograph (e.g., an x-ray image), computed tomography (CT), magnetic resonance imaging (MRI), Ultrasound (US), mammogram, positron emission tomography scan (PET), nuclear scan (NM), pathology, endoscopy, ophthalmology, or many other types of medical images. As mentioned above, medical images may be reconstructed and/or rendered from 3D or volumetric image data using methods including multiplanar reformation/reconstruction (MPR), maximum intensity projection (MIP), and/or the like (including, e.g., any Computerized Advanced Processing (CAP), as described below). Images of the present disclosure also include "multi-frame" images, which are images comprising multiple frames (also referred to herein as sub-images). For example, a multi-frame image may be played as a movie (e.g., showing a beating heart, where each frame shows the beating heart at a different point in time).

Modality: A medical imaging method (e.g., a patient who undergoes an MRI is said to have been scanned with the MRI modality).

Image Series (also referred to herein as a "Series"): Any two or more images that are related. Images in a series typically share one or more common attributes, for example, a type of anatomic plane and/or an image orientation. For example, an image series may comprise two or more images of a particular patient that are acquired on a particular date, e.g., different x-ray projections of the chest. A series of contiguous 3 mm axial CT scans of the chest is another example of an image series. A brain MRI scan might include the following series: sagittal T1 weighted images, axial T1 weighted images, axial FLAIR images, axial T2 weighted images, as well as post contrast axial, sagittal and coronal T1 weighted series. An image series of an exam may be identified by its "type" (also referred to herein as a "series type" and/or a "view type"). For example, series may be acquired using different pulse sequences, acquired in different anatomic planes (also referred to herein as "imaging planes"), and/or acquired before or after administration of intravenous contrast material. An image series may be limited to images of a certain modality or may comprise images of multiple modalities. FIG. 3 illustrates an example of an image series 308, as well as example attributes that may be associated with an image series. As shown, the image series 308 includes multiple medical images, such as medical image 312.

Montage: An arrangement of images. In some implementations, a montage may itself be an image which comprises two or more images stitched together into a single image in a particular arrangement. In some implementations, a montage may be a file comprising sufficient information regarding each image of the montage so that the entire montage can be recreated upon display of the montage.

Patient: An individual who undergoes a medical imaging examination.

Medical Imaging Exam (also referred to herein as a "Medical Exam" and/or an "Exam"): A collection of data related to an examination of a patient. May be specific to a particular time or time period. Generally includes one or more medical images and/or image series, montages, reports, notes, graphs, measurements, annotations, videos, sounds or voice data, diagnoses, and/or other related information. May include multiple image series of multiple modalities, volumetric imaging data, reconstructed images and/or rendered images. For example, an exam of a patient may be the brain MRI scan mentioned above, and may include each of the image series obtained on a particular date including: sagittal T1 weighted images, axial T1 weighted images, axial FLAIR images, axial T2 weighted images, as well as post contrast axial, sagittal and coronal T1 weighted series. Another example of an exam may be a dual-energy radiography exam, which may include image data including traditional x-ray image images, bone subtracted (or "bone out") x-ray images, and/or tissue subtracted (or "tissue out") x-ray images.

Image Characteristic: Any characteristic related to display of an image. Includes without limitation, image angle (e.g., an angle of an image with reference to a standard one or more planes of human anatomy; also referred to herein as "scan plane"), anatomical position (and/or location) (e.g., a location, with reference to a standard one or more planes of human anatomy, of the patient represented in a particular image), image orientation (e.g., an orientation of the image with reference to a standard one or more planes of human anatomy), image rotation (e.g., a rotation of the image with reference to a standard one or more planes of human anatomy), image field of view, slice thickness, image window and/or level (e.g., a contrast of the image, a brightness of the image, and/or the like), image color map (e.g., that includes information for rendering different pixel intensities as different colors), other color characteristics, image opacity (and/or opacity map), image zoom level, image cropping information, and/or the like. In some instances, one or more image characteristics may be user defined and/or based on user preferences. Image characteristics are also referred to herein as image "attributes." Further examples of attributes are described below.

Attribute: Any characteristic associated with a data item (e.g., a data item such as a medical exam, an image series, a medical image, and/or the like). Attributes may be inherited in a hierarchical manner. For example, a medical image may inherit attributes of an image series of which it is a part, and an image series may inherit attributes of a medical exam of which it is a part. Attributes may be stored as part of an associated data item (e.g., as metadata, DICOM header data, etc.) and/or separately from an associated data item.

Image Pane: Also referred to herein as "image frame," "viewing pane," "viewing frame," "comparison pane," "comparison frame," and/or simply "pane." A region of a computer display that may display an image.

Feature: Also referred to herein as an "object." An anatomical characteristic identified in a portion of a medical image, an entire medical image, or a series of medical images that may be of interest to a user (e.g., a radiologist, referring doctor, patient, etc.). Thus, a feature may refer to a lesion, abnormality, or other aspect of a medical image that may be identified manually by a user and/or automatically detected by a computer aided process. In some examples discussed herein, features are associated with individual images. For example, lesions that are automatically detected by a computer aided diagnostic software may be extracted from medical images in which they are identified and each lesion placed in a separate image file Annotation: Any notes, measurements, links, assessments, graphics, and/or the like, associated with a data item, either automatically (e.g., by one or more CAP, described below) or manually (e.g., by a user). For example, when used in reference to a medical image, annotations include, without limitation, any added information that may be associated with the image, whether incorporated into an image file directly, comprising metadata associated with the image file, and/or stored in a separate location but linked to the image file in some way. Examples of annotations include measurements by using linear dimensions, area, density in Hounsfield units, optical density, standard uptake value (e.g., for positron emission tomography), volume, curved lines (such as the length of a curved vessel), stenosis (e.g., percent narrowing of a vessel at a certain location relative to a reference location), or other parameters. Additional examples of annotations include arrows to indicate specific locations or anatomy, circles, polygons, irregularly shaped areas, notes, and/or the like. Additional examples of annotations include arrows to indicate specific locations or anatomy, circles, polygons, irregularly shaped areas, notes, and/or the like. Further examples of annotations include graphics that, for example, outline lesions, lumbar discs, and/or other anatomical features.

User Input (also referred to herein as "Input"): As used herein in reference to user interactions with data displayed by a computing system, "user input" is a broad term that refers to any type of input provided by a user that is intended to be received and/or stored by the system, to cause an update to data that is displayed by the system, and/or to cause an update to the way that data is displayed by the system. Non-limiting examples of such user input include keyboard inputs, mouse inputs, digital pen inputs, voice inputs, finger touch inputs (e.g., via touch sensitive display), gesture inputs (e.g., hand movements, finger movements, arm movements, movements of any other appendage, and/or body movements), and/or the like. Additionally, user inputs to the system may include inputs via tools and/or other objects manipulated by the user. For example, the user may move an object, such as a surgical instrument, tool, stylus, or wand, to provide inputs. Further, user inputs may include motion, position, rotation, angle, alignment, orientation, configuration (e.g., fist, hand flat, one finger extended, etc.), and/or the like. For example, user inputs may comprise a position, orientation, and/or motion of a hand and/or a 3D mouse.

Data Store: Any computer readable storage medium and/or device (or collection of data storage mediums and/or devices). Examples of data stores include, but are not limited to, optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. Another example of a data store is a hosted storage environment that includes a collection of physical data storage devices that may be remotely accessible and may be rapidly provisioned as needed (commonly referred to as "cloud" storage).

Database: Any data structure (and/or combinations of multiple data structures) for storing and/or organizing data, including, but not limited to, relational databases (e.g., Oracle databases, mySQL databases, etc.), non-relational databases (e.g., NoSQL databases, etc.), in-memory databases, spreadsheets, as comma separated values (CSV) files, eXtendible markup language (XML) files, TeXT (TXT) files, flat files, spreadsheet files, and/or any other widely used or proprietary format for data storage. Databases are typically stored in one or more data stores. Accordingly, each database referred to herein (e.g., in the description herein and/or the figures of the present application) is to be understood as being stored in one or more data stores.

This specification describes systems and user interfaces for efficient presentation of medical images of patients and classification of the medical images. In this specification, medical images include any type of image of an organism (e.g., a human patient), and may include, but are not limited to, a radiograph (e.g., an x-ray image), computed tomography (CT), magnetic resonance imaging (MRI), Ultrasound (US), mammogram, positron emission tomography scan (PET), nuclear scan (NM), pathology, endoscopy, ophthalmology, and so on. Additionally, a classification may include any assignment of a quality, characterization, and/or semantic property, to one or more features in the medical images. A feature can include an object of interest, such as a lesion. For example, a classification may include a finding type (e.g., tumor, calcification, malignant, benign), a shape of a feature (e.g., round, oval, heterogeneous), border type, homogeneity, Breast Imaging Reporting and Data System (BIRADS) score, and so on. Additionally, a classification may depend on a passing of time, for example a change in size, character, or other observation, of a feature or object. A quality for an example classification of a shape may include oval shape or round shape. A classification may thus describe a feature (e.g., an object) in a medical image, such as a lesion presented in the medical image.

As described above, medical images can be presented to a reviewing user as a montage, and the reviewing user can classify (e.g., assign classifications) to the medical images. A montage, in this specification, represents multiple medical images (e.g., a collection of medical images). For example, a montage may include medical images that are associated with multiple patients. Optionally, the montage may include medical images of a same type (e.g., mammogram images). Optionally, the montage may include medical images of a same type that illustrate a same feature, for example mammogram images that include lesions. Additionally, the montage may be specific to a particular patient and include medical images of multiple features (e.g., multiple lesions). For example, a montage may include one or more medical images from a multi-image exam (e.g., one or more slices from a multi-image exam).

The reviewing user can view the montage on a user device, such as a computer, tablet, mobile device, and so on, and can select a particular classification to be assigned to one or more of the medical images. For example, the reviewing user can indicate that he/she is going to classify the medical images according to whether a lesion is round or oval. The reviewing user can then rapidly assign the selected classification to medical images with conforming lesions. Since the reviewing user is viewing the montage, the reviewing user can ensure that he/she is consistently classifying medical images. That is, the reviewing user can view the entirety of the medical images included in the montage, and based on analyzing the entire medical images, can more consistently classify them according to same techniques.

As will be described below, the montage can be presented in a user interface as a matrix (e.g., grid). For example, the medical images included in the montage can be presented adjacent to each other, such as a grid (e.g., an M×N grid, where M and N are integers), such that the reviewing user can view the entirety of the medical images. Optionally, a size of the grid can be based on parameters associated with a display being utilized by the reviewing user. For example, a tablet may include a smaller grid than a larger external display. Additionally, a size of each medical image may depend on a display being utilized. In this way, a tablet may include smaller medical images to increase a quantity of medical images that can be included in a montage. Additionally, each medical image can be constrained in how small, or large, the medical image can be. For example, a tablet may present smaller medical images than an external display, but may constrain how small the medical images can be and may therefore limit a size of a grid presented on the tablet.

In the above-described example of the grid, the reviewing user can select a particular classification. For example, and as described above, the reviewing user can indicate he/she is to classify medical images according to shape (e.g., a shape of a lesion is round). In this way, the reviewing user can rapidly classify each medical image according to whether an included lesion is round. Subsequently, the reviewing user can classify medical images according to a different classification. As an example, the different classification may indicate calcification of a lesion. Upon selection of this different classification, the reviewing user can rapidly classify the medical images according to calcification. This focus on classifying the medical images according to a singular classification at a time can improve accuracy of the classification. For example, instead of a reviewing user analyzing individual medical images and assigning disparate classifications to the individual images, the reviewing user can quickly hone his/her focus on a single classification and mark appropriate medical images in a presented montage.

A montage may also be presented as a stack. For example, the medical images included in the montage can be presented on top of each other, and a reviewing user can quickly riffle through the stack classifying the medical images. With respect to the example above of classifying according to shape, the reviewing user can review a top medical image, and utilizing a touch-based user interface, swipe the top medical image in a direction corresponding to a lesion shape being round.

For example, the reviewing user can swipe in a first direction (e.g., right) if a medical image is to be classified according to the selected classification. Alternatively, the reviewing user can swipe in a second direction (e.g., left) if the medical image is not to be classified according to the selected classification. Optionally, a user interface can illustrate an animation of the medical image being swiped according to the direction. Optionally, for a medical image classified according to the selected classification, the user interface can present the medical image in a grid adjacent to other medical images similarly classified from the montage. In this way, the reviewing user can view medical images he/she previously classified according to the selected classification.

Similar to the above-description of a grid, the reviewing user can select a classification and then classify the medical images as corresponding to, or not corresponding to, the selected classification. Since the medical images are in a stack, the reviewing user can quickly cycle through the medical images while, for example, not relocating his/her eyes away from the medical image stack. The reviewing user can select disparate classifications until all of the medical images have been classified. For a subsequent classification selected by the reviewing user, the medical images may be reformed into the stack so that the reviewing user can swipe the medical images again. Additionally, if the subsequent classification is related to a same type of classification (e.g., shape), and is associated with a different quality (e.g., an initial classification may be associated with round lesions, and the subsequent classification may be associated with oval lesions), the montage may include only medical images that have not yet been classified.

Control images may optionally be included in a montage, with a control image known to be of a particular classification. For example, a control image may include a lesion known to be of a particular shape (e.g., round). A control image can be included in a montage to provide a framework for a reviewing user. That is, the control image can be utilized to compare with other medical images included in the montage. Additionally, a control image can be included in a montage to validate credentials of a reviewing user. For example, a reviewing user may be a medical professional (e.g., a doctor) who is required to have undergone particular training. The control images can be included to monitor the reviewing user's performance. If the reviewing user incorrectly classifies a threshold number of control images, the classifications from the reviewing user can be discarded. Additionally, a notification may be generated for transmission to a user identifying the misclassifications. For example, the notification may cause activation of an application executing on a device (e.g., smart phone) of the user. In this way, the user can contact the reviewing user or take other remedial actions. As an example, earlier classifications performed by the reviewing user can be discarded or flagged as requiring review from a different reviewing user. Optionally, as a reviewing user classifies a control image, the reviewing user can receive dynamic feedback indicating whether the control image was classified correctly. For example, a user interface presenting the control image can update to reflect a correct or incorrect classification.

Additionally, and as described above, the control images can inform a final classification that is to be assigned to each medical image. For example, each medical image may be required to be reviewed by a threshold number of reviewing users. If there are discrepancies in the assigned classifications, for example if a system described herein (e.g., the medical image classification system 100) determines different classifications, each reviewing user's accuracy with respect to the control images can be evaluated. Optionally, a weight can be applied to each user's classification based on his/her accuracy with respect to the control images, and a final classification can be assigned based on a combination of these weights. For example, if two reviewing users who are relatively accurate with respect to the control images indicate that a lesion is oval, and one or more other, less accurate, reviewing users indicate the lesion is round, a final classification may correspond to the lesion being oval. Optionally, medical images that are not weighted within a threshold of a particular classification may be discarded. In this way, the classified medical images provided as training data to machine learning system can be ensured to be accurate.

A machine learning system can ingest classified medical images, and utilize the classified medical images as ground-truth or training data. For example, a neural network can utilize the classified medical images to update weights associated with connections between neurons. As another example, a support vector machine can update a generated model.

Figure 2A:
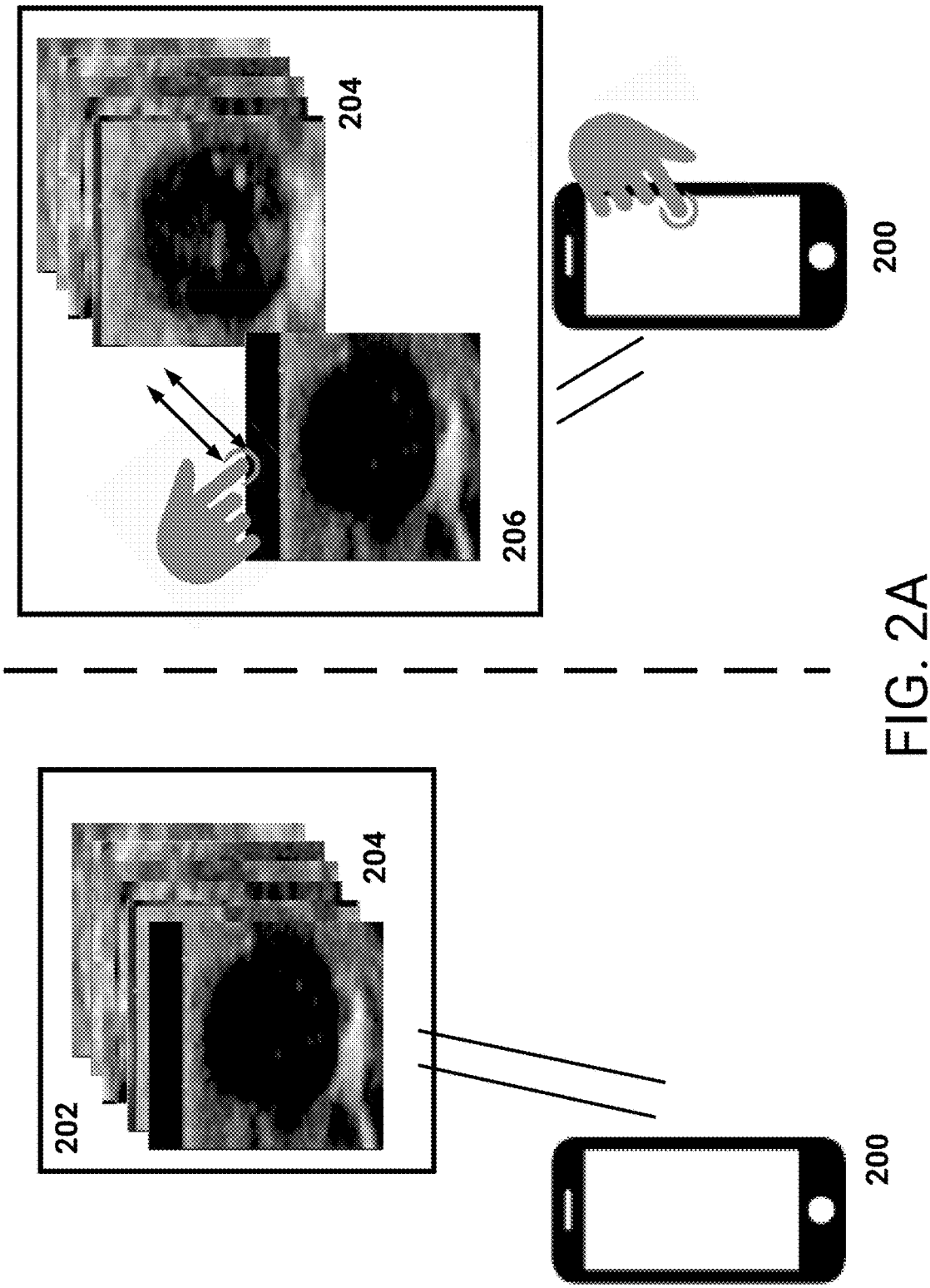
FIG. 2A illustrates an example user interface for classifying medical images.
Figure 2B:
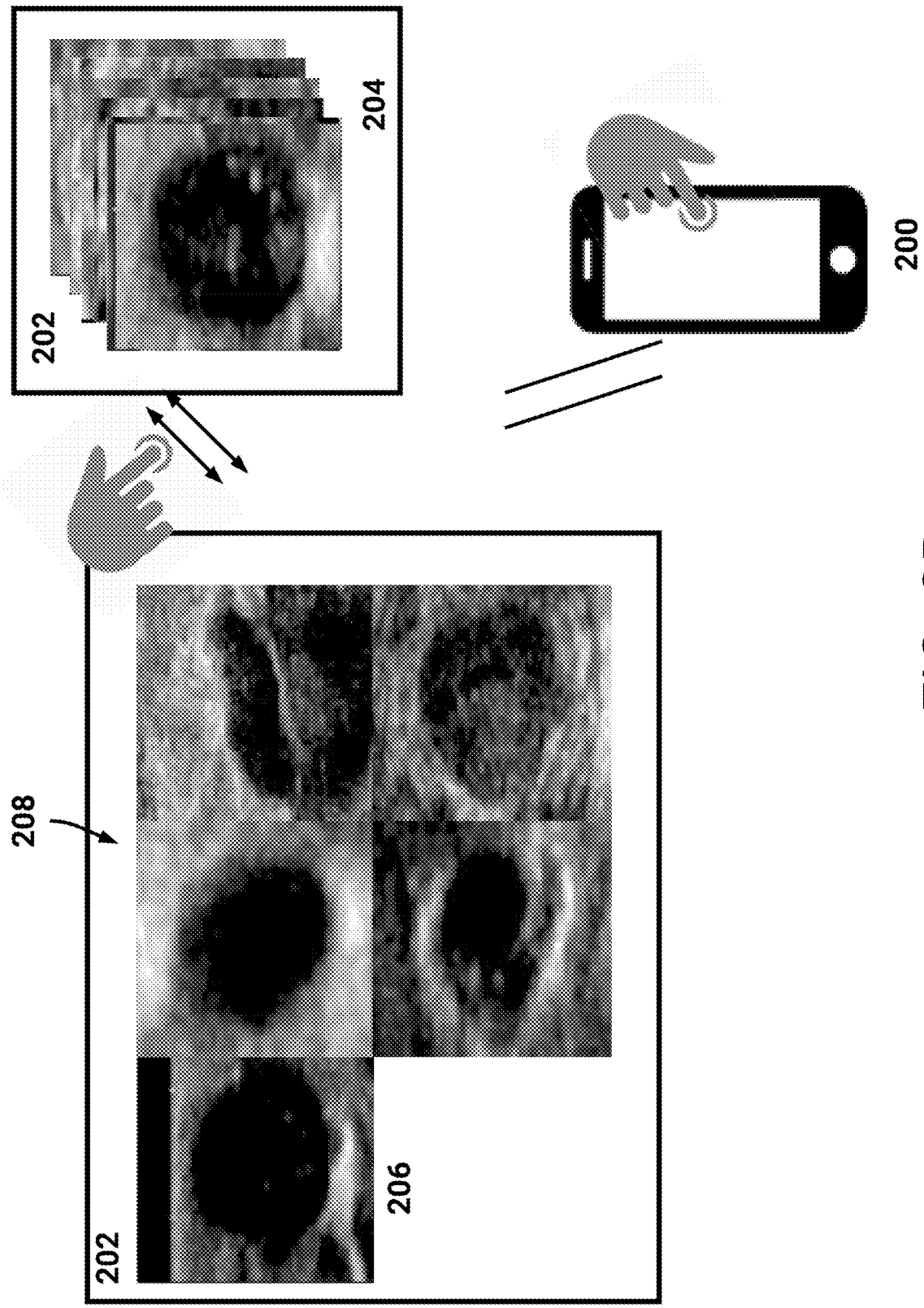
FIG. 2B illustrates another embodiment of the example user interface.

In this way, a reviewing user can classify medical images without any knowledge about patients or exams undergone by the patients. For example, the reviewing user can classify a lesion with regard to a perceived risk of malignancy. As illustrated in FIG. 2D, the reviewing user can drag medical images illustrating lesions onto particular portions of a user interface (e.g., buckets) representing respective levels of malignancy risk. Optionally, the reviewing user can be presented with limited information about one or more patients, for example risk information (e.g., described below), demographic information, medical history, and so on.

Additionally, computer aided diagnostics and/or other machine learning may be used to provide an initial classification for use in any of the example embodiments discussed herein. Thus, prior to medical images being first presented to the user, the images may be classified based on risk conditions (e.g., risk of lymphoma, risk of Crohn's disease, risk of virus, etc.), or other association (e.g., whether a medical image is an anomaly, for example in a group of medical images of a same lesion, or is associated with a defect on a medical instrument, such as an industrial radiograph), which are assigned automatically by the automated diagnostics of a computing system. For example, the computing system (e.g., WATSON) may utilize a risk assessment model to assign an initial classification, or determine an initial risk condition, for an object included in a medical image. As described above, the risk condition may indicate a risk of a particular medical condition, and/or may also indicate an association such as a defect on a medical instrument (e.g., x-ray images may include defects caused by instrument error, and may be discoverable via edge detection, wave profile analyses, segmentation techniques, and so on).

In some embodiments, a risk score for each feature or object may be calculated by the computing system and provided to the user, such as along with display of a medical image. As an example, a system (e.g., the medical image classification system 100, or a machine learning system 130, such as WATSON) may analyze medical records associated with a patient and determine a risk score associated with the patient having a particular medical condition. As another example, the system can analyze medical images of the feature, and determine a risk score associated with the feature. For example, the system can analyze mammogram medical images and assign a risk score to each identified lesion corresponding to a BIRADS score. The reviewing user can utilize the risk score to further classify the feature or object. Such automated classification may optimize further classifications of features by limiting the initial risk categories based on the past medical history of the particular patients, for example. Thus, a particular lesion may be indicative of one or more of four different risk categories (e.g., diagnoses) based on medical imaging characteristics of the lesion alone, but when past history of the patient is considered, one or more of the four different diagnoses may be eliminated as a possibility.

With respect to the example of a classification being associated with a different association than risk, for example a defect on a medical instrument, the system (e.g., system 100, 130) can analyze an image and assign a likelihood associated with a defect. For example, the system can utilize machine learning techniques to identify potential defects, or identify indicia characteristics of a defect (e.g., computer vision techniques). A reviewing user can then utilize this assignment to inform his/her classification of the medical image, such as whether to discard the medical image.

To increase effectiveness of a presented risk score, the system can monitor user performance (e.g., as described above), and determine (e.g., learn) when to present the risk scores associated with medical images to a reviewing user. For example, the system can determine to frontload the reviewing user with positive cases (e.g., cases for which a risk score indicates a positive or likely occurrence of a medical condition), or distribute them evenly, or to never or always provide the reviewing user with information about clinical risk, or never or always provide the reviewing user information regarding imaging risk, or a combination thereof.

As will be described below, with respect to FIGS. 5-7, a subsequent review can be performed of classified medical images. For example, an initial reviewing user, or optionally a machine learning system trained on classified medical images, may assign classifications to medical images. A subsequent reviewing user can view two or more montages, with each montage being associated with a respective classification, and can cause images from a first montage to be included in a second montage. For example, the subsequent reviewing user can view a first montage with objects (e.g., lesions) classified as being round, and a second montage with objects classified as being oval. The subsequent reviewing user can then drag one or more medical images to a different montage, thus classifying the objects as being the other shape. Since the two montages are presented in a same user interface, the reviewing user's effectiveness with respect to ensuring consistency of classification can be increased.

Reports may be generated that can provide an analysis of the medical images classified by a reviewing user. As an example, the system may generate annotations for medical images classified by a reviewing user. That is, a medical report can be generated for a patient that indicates a classification of objects included in medical images related to the patient. As another example, a report can indicate a correct classification of control images. As another example, a report can indicate an amount of time spent on reviewing medical images in each montage, a time (e.g., day, time during the day, and so on) associated with the classification, and so on. A report may further include demographics associated with patients whose medical images were in a montage, and further image characteristics (e.g., breast density). These image characteristics may optionally be automatically extracted or determined via one or more machine vision techniques. For example, a machine vision technique may analyze a medical image and calculate breast density based on identification of fibrous or glandular tissue as compared to identified fat. Optionally, risk classification information associated with the patients, such as the risk score information described above, may be included.

A report may be customized based on a request received from a user. For example, a user may request a report be generated that includes information associated with a particular reviewing user (e.g., particular doctor). This generated report can include summary information associated with the particular reviewing user. As another example, a user may request a report associated with a particular reviewing user and a particular time period. A request may also specify that information from a particular montage be included, or information from any montage that included medical images associated with a particular patient.

As will be described below, a system described herein (e.g., the medical image classification system 100) can store, and enable access to, medical images associated with multitudes of patients. A reviewing user can obtain one or more montages of medical images to be classified, for example via a network call from his/her user device to the system, and indicate classifications assigned to these medical images. The system can then store the classifications. Optionally, access to personal information (e.g., identifying information) associated with patients can be constrained. For example, reviewing users may be able to classify medical images, but be unable to view patient information associated with the medical images. The system can optionally train a machine learning algorithm, or can provide classified medical images (e.g., anonymized classified medical images) to an outside system as training data.

In some embodiments, the features described herein can be implemented as a game or contest. For example, different reviewing users may receive scores or accolades depending on a number of medical images they review. As another example, the medical images may be control images, and reviewing users may be assigned scores based on their performance (e.g., correctness in classifying the control images). Optionally, these medical images may be classified by non-medical personnel, for example with respect to classifying an object based on shape (e.g., round, oval, a d so on). In this way, the techniques described herein can enable crowd-sourcing of classification, annotation, and so on.

FIG. 1 illustrates an example of a medical image classification system 100. The medical image classification system 100 can be a system of one or more computers, one or more virtual machines executing on a system of one or more computers, and so on. As described above, the medical classification system 100 can store, or enable access to, medical images stored in a medical image database 110. The medical image classification system 100 can provide medical images 102, for example in a montage, to a user device 120 of a reviewing user 122, and receive classified medical images 104 in response. For example, a classified medical image may include an associated medical image along with metadata describing the classifications.

Medical image database 110 can store medical images associated with multitudes of patients, such as hundreds, thousands, hundreds of thousands, and so on. These medical images may optionally be anonymized to remove personal information related to the associated patients. Additionally, medical images stored in the medical image database 110 can be opt-in. For example, patients can affirmatively indicate that their medical images can be utilized. Optionally, medical images 102 obtained from the medical image database 110, which are provided to the reviewing user 122, can be stripped of personally identifiable information prior to transmission to the user device 120.

The medical images stored in the medical image database 110 can be analyzed, and particular features (e.g., objects) can be extracted and marked or otherwise highlighted. For example, a medical image that is a mammogram can be analyzed, and a lesion included in the medical image can be marked. The lesion may be extracted from the mammogram, such that a medical image of the lesion which will be reviewed by a reviewing user includes a portion of the larger medical image (e.g., the immediate area surrounding the extracted lesion). This analysis can optionally be performed by a reviewing user. For example, the reviewing user can view each medical image and indicate a boundary associated with an included feature (e.g., a lesion). The analysis may optionally be performed by a machine learning system. Additionally, computer vision techniques can be utilized to identify the boundary. For example, an edge detection scheme can be utilized to determine the boundary. As another example, a shape detection scheme can be utilized to identify shapes associated with the feature (e.g., shapes of lesions).

As an example of a marked or otherwise highlighted medical image, example medical images 124A, 124B, are mammograms. Each example medical image 124A, 124B, includes a highlighted border 126A, 126B, of a particular extracted feature (also referred to herein as an "object"). In the example of FIG. 1, the particular feature is a lesion and the border represents an extremity of the lesion. As will be described in more detail below, a reviewing user (e.g., reviewing user 122) can review each example medical image 124A, 124B, and determine classifications for the included features (e.g., features 126A, 126B). For example, the reviewing user can determine whether feature 126A is to be classified as round or oval.

Therefore, the medical image database 110 can store medical images with disparate features highlighted otherwise identified for review by reviewing users. Additional features may include tumors, indications of breast density, bone fractures, and so on.

As described above, the medical image classification system 100 can provide a threshold number of medical images 102 for presentation on the user device 120 of the user reviewing user 122. The threshold can be based on display size associated with the user device, and can include upper and/or lower bounds. For example, the medical images 102 received by the user device 120 can be presented as a montage to the user 122. The montage may be constrained to include no greater than a particular number of medical images (e.g., 20, 30, and so on), and may be constrained to include no less than a particular number (e.g., 2, 6, 10, and so on). Optionally, the reviewing user 122 can indicate his/her preference regarding a number of medical images 102 to be included in a montage.

Optionally, the number of medical images 102 to be included in the montage can be determined (e.g., learned) by the user device 120 or the medical image classification system 100. The determination may be based on an amount of time the reviewing user takes to classify medical images along with a number of medical images (e.g., a classification of a medical image per unit of time can be determined). A number of medical images can be preferred that minimizes the amount of time the reviewing user 122 is determined to spend on each medical image.

Additionally, the determination may be based on performance associated with classifying the medical images. For example, control images may be included in the medical images 102, and if the device 120 or system 100 determines that more than a particular number of medical images results in worse classification of the control images by the reviewing user 122, the particular number can be preferred. For example, as the number of medical images increases, the montage may appear cluttered and the reviewing user 122 may be less able to properly classify the medical images. Similarly, medical images may be classified multiple times by differing reviewing users. In this way, the classification finally assigned to each medical image may be determined based on multiple classifications. Each reviewing user's performance can be based on his/her initial classification of a medical image to a final classification of the medical image. A number of medical images in a montage can be varied for the reviewing user 122, and his/her performance monitored. In this way, the number of medical images included in a montage can be tailored for this reviewing user 122.

Figure 3A:
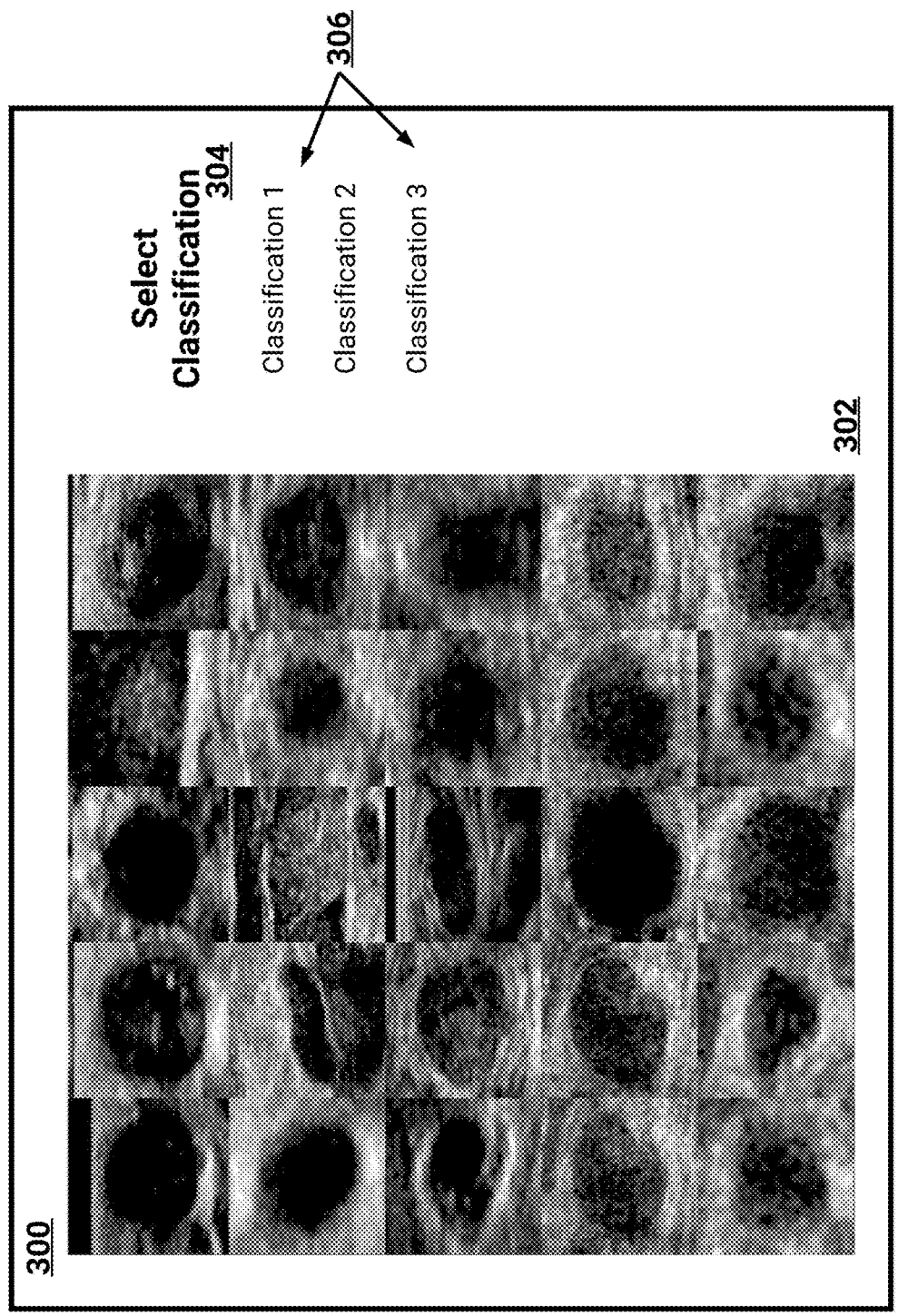
FIG. 3A illustrates an example of a user interface for classifying medical images
Figure 3B:
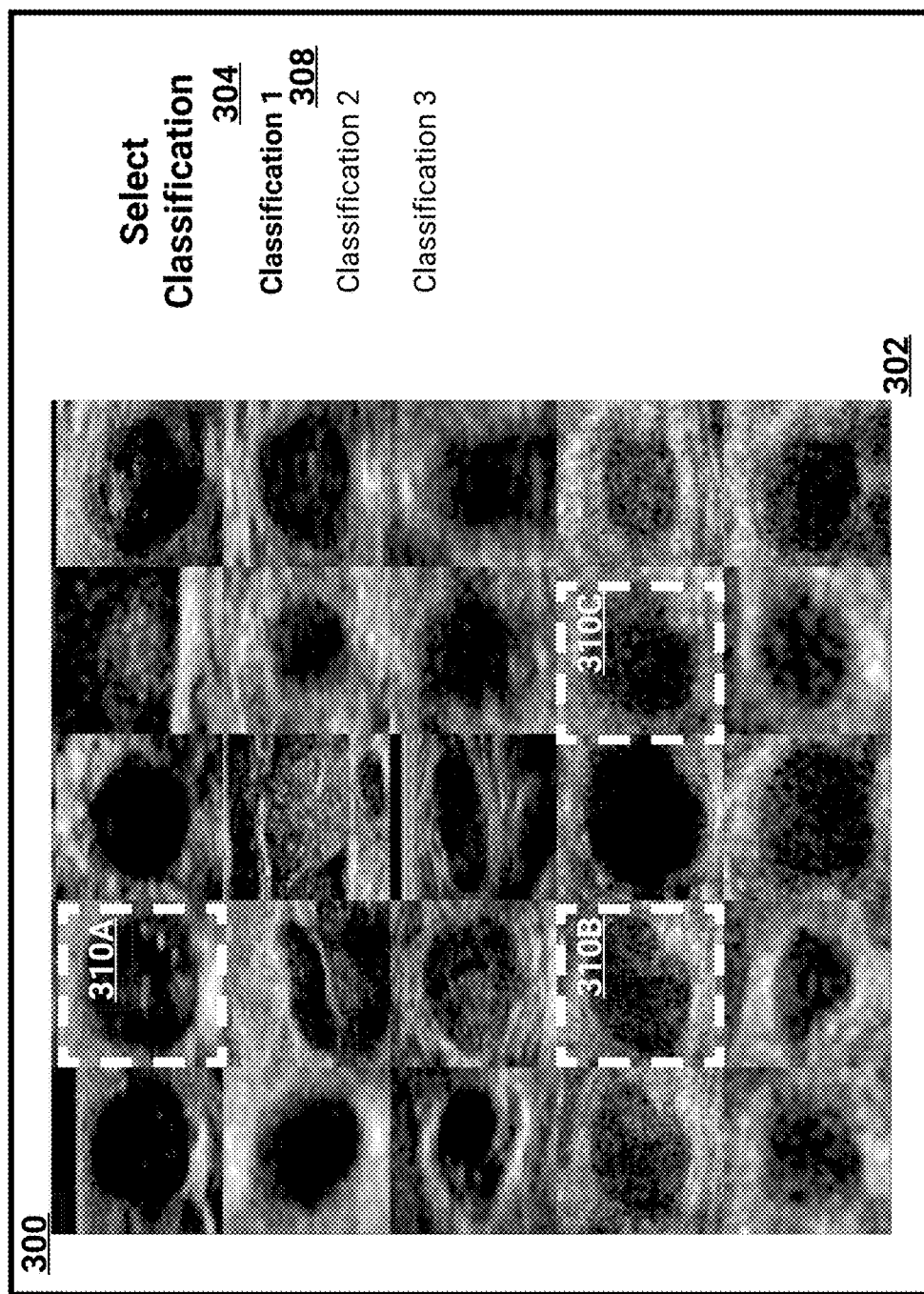
FIG. 3B illustrates the user interface with classified medical images.

As will be described in more detail below, with respect to FIGS. 2A-2B and 3A-3B, the reviewing user 122 can classify each received medical image 102. For example, the reviewing user 122 can view a montage of medical images 102, and classify each medical image. The montage can be presented as a stack (e.g., as illustrated in FIGS. 2A-2B), or as a grid (e.g., as illustrated in FIGS. 3A-3B). Classification, as described above, can include each medical image being assigned one or more classifications by the reviewing user 122. For example, the reviewing user 122 can indicate that a lesion (e.g., lesion 126A) in medical image 124A is round as a first classification. Optionally, the reviewing user 122 can indicate an additional quality related to the medical image 124A.

The medical image classification system 100 can receive the classified medical images 104, and store the medical images 104. For example, the medical image classification system 100 can update the medical image database 110. Optionally, the received classified medical images 104 may be associated with the reviewing user 122. For example, metadata may be generated and included with the classified medical images 104 identifying the reviewing user. As another example, one or more database tables may be updated to reflect the classification (e.g., unique identifiers of the medical images 102 can be associated with the reviewing user 122 and/or unique identifiers of the classified medical images 104).

In this way, the medical image classification system 100 can monitor the medical images reviewed by each reviewing user. As described above, the system 100 can require that each medical image be classified by a threshold number of reviewing users to ensure accuracy of the classification before use of the classification in training of a machine learning system. The system 100 can therefore track a number of times each medical image was classified, and can generate reports related to the classification and/or a reviewing user.

Thus, medical images can be accurately classified by reviewing users. The classified medical images can be provided to a machine learning (ML) system 130 for training, with the machine learning system 130 having a greater assurance of accurate training. Optionally, the medical image classification system 100 may implement the machine learning system 130. Optionally, the machine learning system 130 may be associated with deep learning, such as WATSON.

As described above, a classification of a medical image may be associated with a diagnosis regarding a medical condition. For example, a medical image may be classified as illustrating a malignant tumor. As another example, a medical image may be classified as illustrating Crohn's disease, and so on. To inform a proper classification regarding a diagnosis, a risk score related to a medical condition can be generated by the system 100 or machine learning system 130. The risk score can represent a respective risk class of a patient having the medical condition, for example a BIRADS score.

As illustrated, a medical record database 116 is included in FIG. 1. The medical image classification system 100 may have access to medical records of patients that are stored in the database 116, and which may inform a determination of such a risk score. For example, medical images of breast lesions may be analyzed, and a determination of a risk related to breast cancer determined (e.g., a BIRADS score may be determined by system 100, 130, based on analyzing a medical image). To further inform the risk score, medical records associated with patients can be analyzed. For example, history information, demographic information, clinical notes, and so on, can be analyzed. The system 100, 130, may utilize deep learning, natural language processing, natural language understanding, and so on, to determine a risk score. While risk score is described herein, it should be understood that a risk score can be represented as a textual description (e.g., label) applied to a medical image. For example, a risk score may indicate that inflammation indicates a threshold risk of a virus, or a threshold risk of Crohn's disease, and so on.

In the example of a BIRADS score, the system 100, 130, can review a patient's medical history for indicia of breast cancer. Similarly, a patient may complain of bowel troubles, and the system 100, 130, can analyze his/her medical records for information related to a diagnosis. As an example, if the patient is young and has not previously complained of such troubles, the system may determine that Crohns disease is unlikely as compared to a virus. The system may further analyze information indicating the patient traveled to a particular region in which such a virus is found. Therefore the system can assign a risk to medical images of the patient as indicating a risk for a virus. Thus, a reviewing user can utilize this initially determined risk of a virus when reviewing the medical images, thereby not reviewing in a vacuum but with initial knowledge. As will be described, the reviewing user can update the classification to be, for example, Crohns disease based on analyzing the medical image and/or medical history.

Subsequently, medical images can be grouped according to risk score. For example, medical images of breast lesions can be grouped by the system 100 according to respective BIRADS score. These grouped medical images can then be included in respective montages, and a reviewing user can classify the medical images according to a diagnosis. As an example, a first montage may include medical images with a BIRADS score of '4'. The reviewing user can review these medical images, and can classify each as representing a cancerous or benign lesion. Additionally, the reviewing user can review these medical images and can classify each as include a round or oval lesion. Thus, the risk score (e.g., BIRADS score) can inform the final classification assigned to each medical image by a reviewing user.

FIGS. 2A-3C illustrate embodiments of user interfaces utilized for classifying medical images. It should be understood that the description included in each figure can be applied to other figures. For example, feature described with respect to a montage being a stack may be applied to a montage being a grid, and so on.

FIG. 2A illustrates an example user interface 202 for classifying medical images. The example user interface 202 can be an example of an interactive user interface generated, at least in part, by a system (e.g., a server system, the medical image classification system 100, and so on), and which is presented on (e.g., rendered by) a user device 200 (e.g., a laptop, a computer, a tablet, a wearable device). For example, the user interface 202 can be presented via a webpage being presented on the user device 200. As another example, the webpage may be associated with a web application (e.g., executing on the medical image classification system 100) that receives user input on the user device 200 and updates in response. Optionally, the user interface 202 can be generated via an application (e.g., an 'app' obtained from an electronic application store) executing on the user device 200, and the application can receive information for presentation in the user interface 202 from an outside system (e.g., the medical image classification system 100).

As described above, a reviewing user can receive medical images, for example in response to a request provided to a system (e.g., the system 100), and classify the medical images. For example, the reviewing user can identify a particular classification (e.g., a shape of a lesion being round), and assign the particular classification to one or more medical images. Subsequently, the reviewing user can identify a different classification (e.g., a shape of a lesion being oval), and assign the different classification to one or more other medical images.

To increase an accuracy associated with such classification, and thus to improve functioning of machine learning systems, medical images can be presented as a montage (e.g., a collection of medical images). FIG. 2A illustrates an example montage 204 being presented in a user interface 202, which is displayed on a user device 200. While the example of FIG. 2A illustrates the user device as being a mobile device or tablet, it should be understood that the user device can be a laptop, a computer (e.g., with an external display), and so on. Optionally, the laptop or external display may be touch-sensitive, enabling the user to directly interact with the example montage 204.

The example montage 204, in the illustrated example, is a stack of medical images. As described above, the medical images may be associated with multiple patients and the reviewing user can interact with the montage 204 to assign classifications to the medical images. As will be described below, the reviewing user can cycle through the reviewing users and assign to one or more medical images a particular classification. For example, the reviewing user can swipe in a first direction (e.g., right) on a medical image to indicate that the medical image is to be classified according to the particular classification, and can swipe in a second direction (e.g., left) to indicate that the medical image is not to be classified according to the particular classification.

The reviewing user can select a particular classification, for example from a presented list, and then cycle through the reviewing images. Optionally, the presented list may include classifications specific to a type associated with the received medical images. For example, received mammogram images may be associated with classifications such as shape of a lesion, density, BIRADS score, and so on. Optionally, the reviewing user may speak a particular classification, and the user device 200 can match the spoken to a particular classification. As an example, the reviewing user can say, "Oval Lesion," and the user device 200 can interpret the speech as corresponding to a shape classification with a quality of oval (e.g., a value of oval for the shape classification). Therefore, the reviewing user can indicate a classification type (e.g., shape), along with a quality associated with the type (e.g., oval, round).

Upon selecting the particular classification, the reviewing user can review an initial (e.g., top) medical image 206. As illustrated, the reviewing user has reviewed the initial medical image 206 and has swiped in a particular direction to indicate whether the medical image is to be assigned the particular classification. While the example of FIG. 2A illustrates swiping, it should be understood that additional input schemes can be utilized. For example, the reviewing user can press with greater than a particular pressure or force on a pressure sensitive screen to indicate that the medical image 206 is to be assigned the particular classification. As another example, the reviewing user can utilize a mouse and/or keyboard to interact with the medical image. In this example, the reviewing user can click, or right click, on the medical image 206, and the user interface 202 can update with selectable options associated with assigning the particular classification. As another example, the reviewing user can verbalize whether the medical image 206 is to be assigned the particular classification.

With respect to the example of swiping, upon swiping of the medical image 206, the medical image 206 can relocate to away from the stacked montage 204. For example, the medical image 206 can move in a direction of the swiping, and a new stack may be initiated. As the reviewing user swipes subsequent medical images from the montage 204 in the same direction, these subsequent images can be placed on top of the initial medical image 206 (e.g., forming a stack). Similarly, as the reviewing user swipes subsequent medical images from the montage 204 in a different direction, the subsequent medical images can form a different stack. In this way, the user interface 202 may include multiple stacks as the reviewing user cycles through the medical images. For example, the user interface 202 may include the stacked montage 204 with medical images requiring classification, a stack of medical images being assigned a particular classification, and a different stack of medical images not being assigned the particular classification. Optionally, the different stack of medical images may not be presented, or the included medical images may be ordered at the bottom of the stacked montage 204.

As illustrated, the stacked montage 204 may optionally present the medical images in a stack slightly offset from each other. In this way, the reviewing user can obtain a quick sense of a remaining number of medical images (e.g., the user interface 202 may also specify a number remaining). Similarly, as the stack of classified medical images (e.g., the stack with medical image 206 at a bottom) forms, the stacked medical images may be offset. Additionally, the user interface 202 can be configured to receive inputs associated with the stack, enabling the reviewing user to again review medical images included in the stack. For example, the reviewing user can swipe on a top medical image of the stack, and the top medical image can temporarily relocate or disappear leaving a different medical image on top of the stack. The reviewing user can swipe away these medical images until he/she locates a particular medical image of interest. The reviewing user can then maintain its assignment in the stack, or can indicate that the particular medical image is to be differently classified (e.g., the reviewing user can swipe the medical image to a different stack, or back into the montage 204 for later review).

FIG. 2B illustrates another embodiment of the example user interface 202. As described above, a stacked montage 204 of medical images can be presented in a user interface 202 displayed on user device 200. As a reviewing user assigns medical images to a classification (e.g., medical image 206), the medical images may be placed in a grid. For example, grid 208 includes medical images classified according to a classification (e.g., selected by the reviewing user). In this way, the reviewing user can quickly review the medical images he/she has classified according to a same classification (e.g., review all medical images he/she has indicated as including an oval lesion).

Figure 2C:
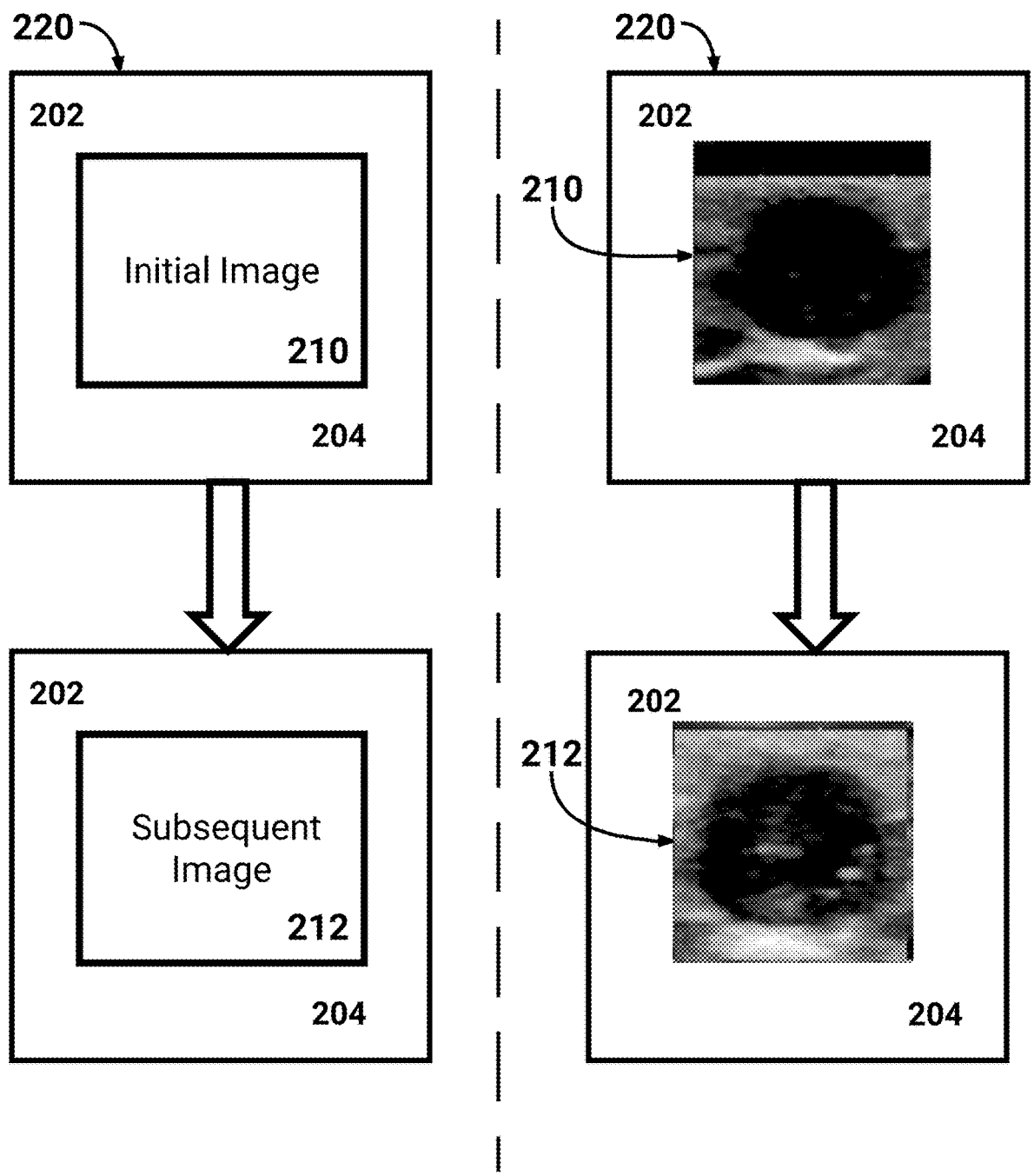
FIG. 2C illustrates another embodiment of the example user interface.
Figure 2D:
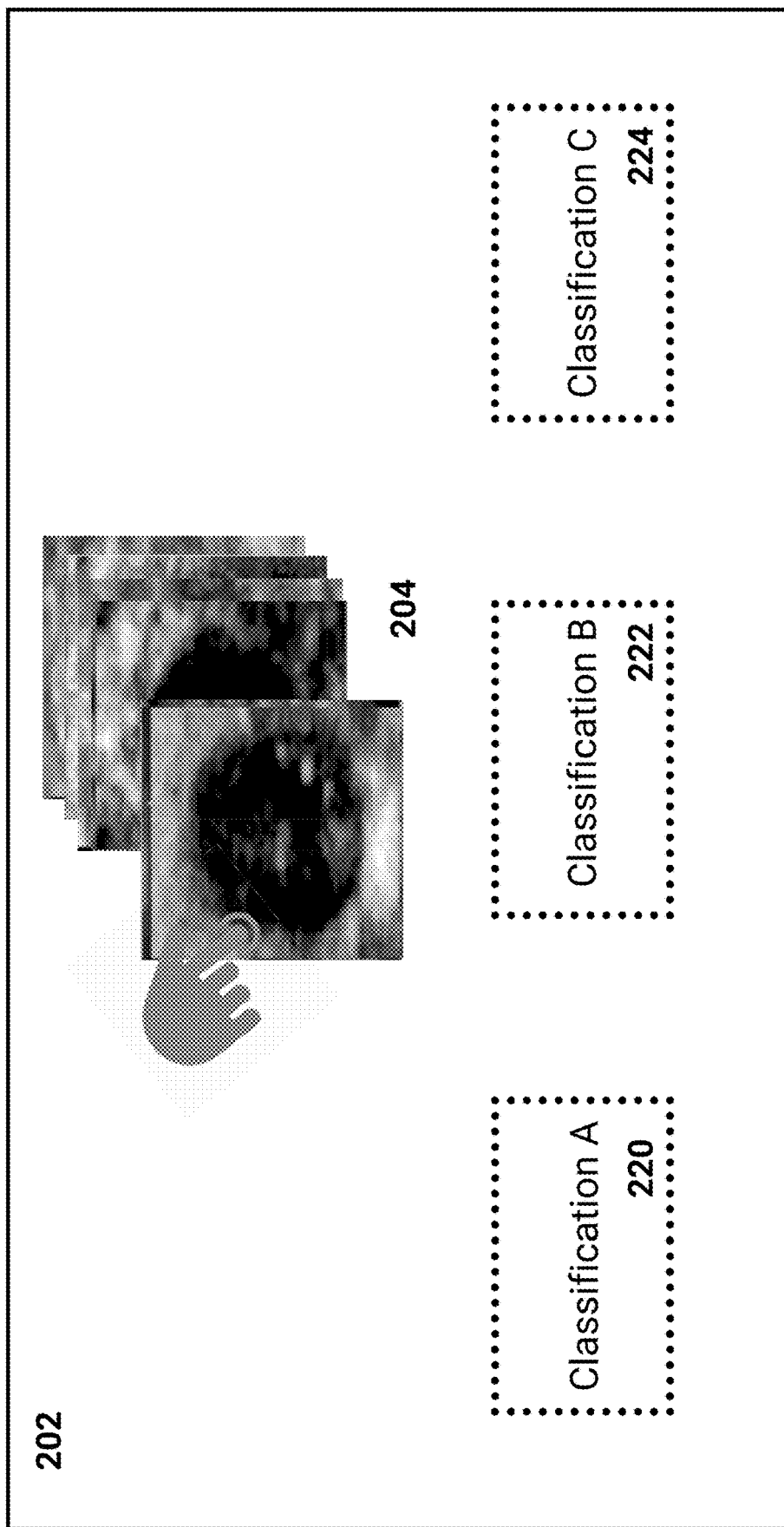
FIG. 2D illustrates another embodiment of the example user interface.

FIG. 2C illustrates another embodiment of the example user interface 202. In this example, medical images included in a display window 220 may be alternatively viewed at a particular location of the screen. For example, in response to a user input (e.g., scrolling up using a scroll wheel on a mouse), or after a threshold amount of time (e.g., 1 second, 3 seconds, a user-selectable amount of time), the user interface 202 can update to replace image 210 with subsequent image 212. In this way, differences between these medical images 210, 212, may be more readily detectable as the user interface 202 cycles through the comparison images. For example, differences in the shapes of features (e.g., objects, such as lesions) included in the medical images 210, 212, and other images in the set of images may be more apparent. In this way, the reviewing user can focus his/her attention on a same location in the user interface. The user can flip back-and-forth between two images to even more easily detect subtle differences in the images and more consistently assign classifications to images by comparing the objects using this "quick-flip" functionality.

In one embodiment, a set of images for viewing in this manner—concurrently in a same display area of the screen—may be selected, either automatically or by the user, to include only images with a same (or similar classification) . Thus, the user can flip through the images (e.g., by scrolling up and down using a scroll wheel or touch-sensitive input device) to confirm that the categorization is consistently applied to all of the images. For example, a set of 20 images that have preliminary been assigned a "circular" classification (either by one or more users or by a computer automated determination) can be sequentially displayed so that any images that may not be as "circular" as the others can assigned a different classification (e.g., changed to "oval"). In some embodiments, the system automatically registers the object in the images so that the size, orientation, window-level, and/or other display characteristics, are consistent across all of the images so that flipping between the images allows easier comparison and/or classification of the objects.

Optionally, the user device 200, or system 100, may store settings for displaying medical images, such as, for example, time for displaying each medical image, resolution of each medical image, cropping to be applied to each medical image, and any other setting that maybe appropriate. In one embodiment, the time for displaying a medical image may be determined real time by the reviewing user. For example, the reviewing user may press a designated key on a keyboard or mouse to indicate that the current medical image should be replaced with a subsequent medical image. In another embodiment, the user can select settings for display of the medical images. For example, the user may select an appropriate zoom level of to be applied to the medical images.

The reviewing user can indicate whether the initial image 210 or the subsequent image 212 is to be classified according to a particular classification, for example as described above. As an example, the reviewing user can utilize a keyboard or mouse to select a medical image. As another example, the reviewing user can verbally indicate whether a medical image is to be classified according to the particular classification.

FIG. 2D illustrates another embodiment of the example user interface 202. In the example, a montage stack 204 is included along with identifiers of classifications that can be assigned to each medical image included in the montage 204. For example, Classifications A-C 220-224 are illustrated. A reviewing user can drag a medical image from the montage stack 204 for inclusion in a determined classification, thus rapidly riffling through the medical images. That is, the reviewing user can drag a top medical image included in the montage 204 onto, for example, Classification A 220. The top medical image can then remain in the user interface portion associated with Classification A 220. Optionally, as additional medical images are dragged onto Classification A 220, a stack of medical images can be formed at 220. Optionally, the additional medical images can form a grid of medical images assigned Classification A 220, for example similar to grid 302 described below.

As described above, the montage 204 may include medical images that are grouped according to risk (e.g., risk score, risk class) and/or by prior classifications provided by other users and/or computer automated classifications. As an example, the medical images included in the montage 204 may have been assigned a particular BIRADS score. The classifications 220-224, included in user interface 202 may be related to a medical diagnosis associated with the BIRADS score. For example, the classifications can indicate whether the medical images represent cancer, e.g., highly likely, moderately likely, or not likely. Another example, classifications may be associated with shape of the features, such as round, oval, or non-uniform. Similar to the above description of control images, optionally control images that include features or objects of a known diagnosis may be included in a montage. As described above, a classification may relate to a change in size or character of a feature or object, such as a lesion. Control images may be included, such as pairs, triplets, and so on, that illustrate a same lesion changing, or not changing, in size or character over time. The control images illustrating a same lesion may be presented as being associated with a same lesion, for example the control images may include textual descriptions indicating they are related, may be highlighted a particular color, and so on. In this way, the reviewing user's performance related to classifying these control images can be monitored.

FIG. 3A illustrates an example of a user interface 300 for classifying medical images. User interface 300, which can be presented on a user device such as described above with respect to at least FIG. 2A, includes a montage 302 of medical images. For example, the montage 302 can be received from a system (e.g., the medical image classification system 100), and presented on a user device of a reviewing user. As illustrated, the montage 302 in this example is represented as a grid of medical images. While a shape of the grid is rectangular, the shape me be circular or optionally in the shape of a person (or portion of person from which the images were obtained). Additionally, medical images can be included in the montage according to their location on a person. For example, medical images illustrating breast lesions in an upper left quadrant of the breast may be included on the upper left quadrant of the montage, with an outline of the breast underlaid behind the images to provide context of the image location. Optionally, a montage grid may include stacked medical images. For example, a particular quadrant of the montage 302 may include multiple images that are stacked. In this example, the montage may optionally be shaped like a human (or portion of a human), with each image set including medical images related to a portion of the human at which the image set is position in the user interface.

In contrast to the example user interface 202 of FIG. 2A, 2B, the user interface 300 can enable a reviewing user to quickly select a classification 304, and indicate medical images from the montage 302 that are to be assigned a selected classification. As illustrated, multiple classifications 306 are presented (e.g., classification 1-3), and the user can select a particular classification from the presentation. Optionally, the classification 304 may represent a type of classification, such as shape, and the multiple classifications 306 may be qualities or values of the type (e.g., round, oval, heterogeneous). FIG. 3B illustrates the reviewing user as having selected a particular classification 308, and interacted with user interface 300 to indicate medical images that are to be assigned the classification 308 (e.g., medical images 310A-310C).

FIG. 3B thus illustrates the user interface 300 with classified medical images. Upon selection of a particular classification, for example 'classification 1' 308 as illustrated, the reviewing user can indicate medical images that are to be assigned the classification 308. For example, the reviewing user can long-press (e.g., press for greater than a threshold amount of time), press with greater than a threshold force or pressure, or press, on a touch sensitive screen illustrated user interface 300. Additionally, the reviewing use can utilize a mouse and/or keyboard to select (e.g., click on) a medical image to indicate its classification, or can provide verbal commands (e.g., speech) indicating a classification. In this way, the reviewing user can indicate that medical images 310A, 310B, 310C, are to be classified according to the selected classification 308.

Once the reviewing user completes assigning the selected classification 308, the reviewing user can select a different classification (e.g., 'classification 2'), and assign one or more other medical images in the montage 302 to this different classification. Upon assigning each medical image in the montage 302 to a classification, the reviewing user's user device can cause storage of the classifications (e.g., by the medical image classification system 100).

Figure 3C:
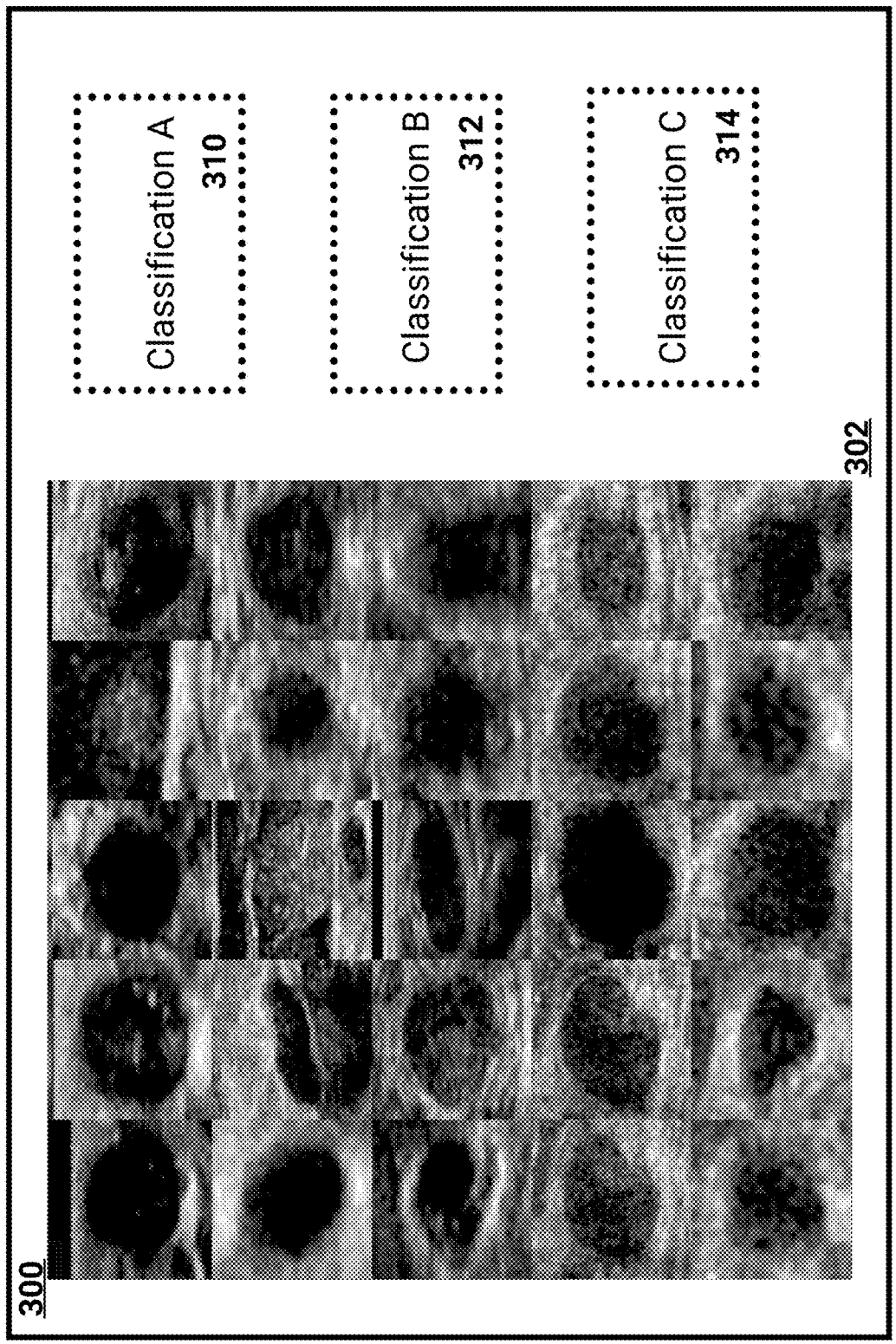
FIG. 3C illustrates another embodiment of an example user interface for classifying medical images.

FIG. 3C illustrates another embodiment of an example user interface 300 for classifying medical images. Similar to FIG. 2D, disparate classifications A-C 310-314 are illustrated in user interface 300. The reviewing user can drag a particular medical image onto a particular classification to classify the particular medical image.

Figure 4:
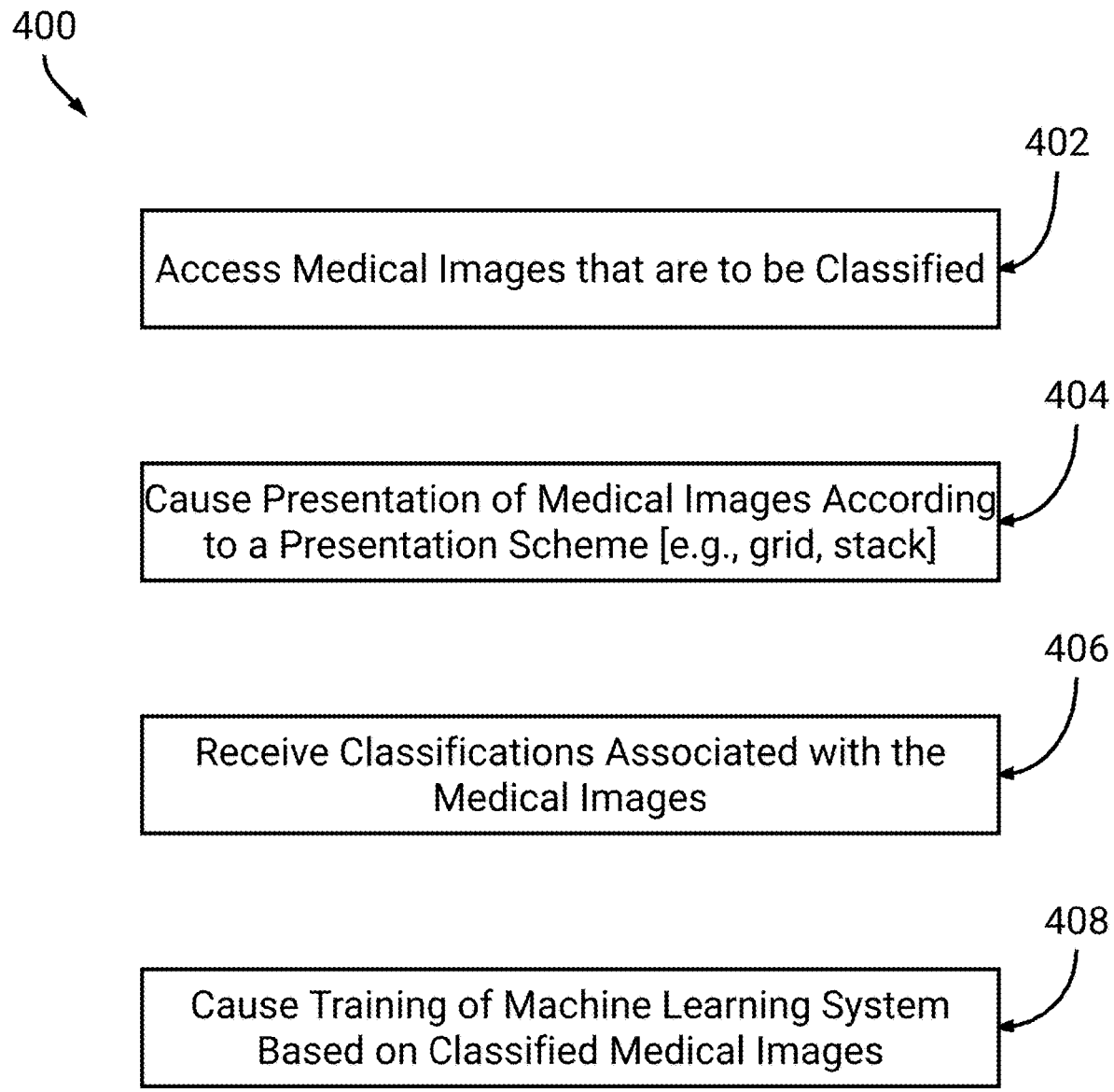
FIG. 4 illustrates an example process for training a machine learning system based on classified medical images.

FIG. 4 illustrates an example process 400 for training a machine learning system based on classified medical images. For convenience, the process 400 will be described as being performed by a system of one or more computers (e.g., the medical image classification system 100).

The system accesses medical images that are to be classified (block 402). As described above, a reviewing user can request a montage of medical images, for example via his/her user device, and the system can access medical images in response. The system can identify any medical images that have yet to be classified, or can identify medical images that have been classified by less than a threshold number of reviewing users.

The system causes presentation of the medical images according to a presentation scheme (block 404). As illustrated in FIGS. 2A-2B and 3A-3B, the medical images can be presented as a montage according to different presentation schemes. For example, the montage can be presented as a stack, or as a grid. The reviewing user can optionally indicate on his/her user device a preferred presentation scheme, and can optionally switch back and forth between presentation schemes.

Optionally, the reviewing user can request more detailed information related to some, or all, of the medical images. As an example, the reviewing user can request (e.g., via a user input, such as clicking on a particular medical image of the montage showing an object that is part of a larger medical image) that more/all of the medical image surrounding the displayed medical image be presented. The system could display the medical image in the same or separate image pane, and return to the montage of images in response to the user providing another input (e.g., clicking on the expanded medical image).

As another example, the reviewing user can request patient information to inform his/her determination of a classification. For example, a determination as to a lesion being suspicious (e.g., cancerous) can be informed by an associated patient's history. Optionally, the montage may include multiple views of a same feature included in a medical image. For example, a particular lesion may be presented in differing medical images, such that the reviewing user can view the particular lesion from differing perspectives or views. Additionally, the montage may include a same feature as imaged in multiple exams, for example multiple exams performed on a same day or within a threshold period of time. As an example, a particular lesion may be presented in differing medical images, with the medical images being from differing exams. The montage may further be specific to a particular patient, or two or more patients, with multiple medical images being associated with each patient. This example montage may therefore include medical images of differing features associated with each patient, for example multiple lesions of a same patient. As a further example, a montage may present medical images of a lesion of a particular patient, with the medical images being taken at different points in time. The reviewing user can determine whether the lesion is changing in size or character, and the classifications can indicate points in time at which the lesion changes. In this example, risk information may be determined (e.g., as described above) for the medical images of the lesion. The risk information may indicate information associated with a change in the montage, for example as compared to a prior medical image of the lesion. A system (e.g., WATSON), may analyze the medical images and indicate a measurement associated with a change of each medical image as compared to one or more prior medical images. For example, a measurement can be based on a size of the lesion, density, or other quality.

Additionally, the medical images may be associated with a same risk of a particular medical diagnosis. As described above, with respect to FIG. 1, medical images may be included in a montage that are specific to a particular risk score or risk class. The reviewing user can review these medical images, and classify them according to diagnosis and/or other classifications. As an example, a montage may include medical images assigned a particular BIRADS score, and the reviewing user can indicate whether the medical images include objects that appears to be cancerous or benign. In some embodiments, the medical images of a montage may be sorted based on a risk or, such as placing an image with the highest BIRADS score at the upper left location of a montage and an image with the lowest BIRADS score at the lower right location of the montage. To help viewers make further classification determinations, the particular BIRADS score may be helpful—thus increasing classification accuracy. Additionally, the reviewing user can indicate that the initial risk assigned to the medical image is incorrect. For example, the reviewing user can indicate that a different BIRADS score should have been determined for the medical image. A machine learning system that assigned the BIRADS score can receive this update, and training of the system can be performed, such that later automated classifications of similar images are more appropriately assessed and/or reassessment of already classified images may be performed.

As an example, a montage may include medical images indicated as including objects that are malignant, for example based on a machine learning system (e.g., WATSON) analyzing the medical images and/or medical history of patients. In this example montage, the reviewing user can assign a BIRADS score as a classification. For example, with respect to FIG. 2D, the reviewing user can drag and drop medical images onto different classifications associated with respective BIRADS scores. As another example, a montage may include medical images associated with patients assigned a particular risk for cancer. In this example, the reviewing user can classify the medical images as including objects that are malignant or benign. In this way, if the reviewing user can view a risk of cancer, the reviewing user may be more effective at classifying a medical image Returning to FIG. 4, the system receives classifications associated with the medical images (block 406). As described above, the reviewing user can indicate classifications that are to be applied to the medical images. For example, the reviewing user can select a particular classification (e.g., shape), and then a particular quality associated with the particular classification (e.g., oval, round), and assign one or more medical images to this classification. The system can receive these classifications, and store the classifications. Optionally, the stored classifications can be associated with the reviewing user, and for example reports can be generated as described above.

The system causes training of a machine learning system based on the classified medical images (block 408). The system can utilize the classified medical images to train a machine learning system, for example using the classified medical images as ground-truth or training data. Optionally, the system can ensure that each medical image has been classified a threshold number of times, and can determine a final classification for each medical image as described above.

The description above, with respect to FIG. 1-4, focused on a reviewing user classifying medical images utilizing efficient user interfaces. As these user interfaces increase an ability of the reviewing user to correctly and consistently classify medical images, an accuracy of a machine learning system can be enhanced. To further increase accuracy of the classified medical images, a reviewing user can view two or more montages of differently classified medical images, and re-classify them. For example, the two or more montages may include objects of a same type (e.g., breast lesions), which have been differently classified (e.g., oval or round). The reviewing user can rapidly review these montages, and can, for example, drag a medical image included in a first montage for inclusion in a second montage. As described above, a re-classification may be based on an observation related to changes in a feature or object (e.g., lesion) over time. As an example, a change in size or character over time may be a classification. For example, a first montage may include medical images of a particular lesion taken at a particular time, and a second montage may include medical images of the particular lesion taken at a subsequent time. In this way, the reviewing user can easily view differences in the lesion.

Figure 5:
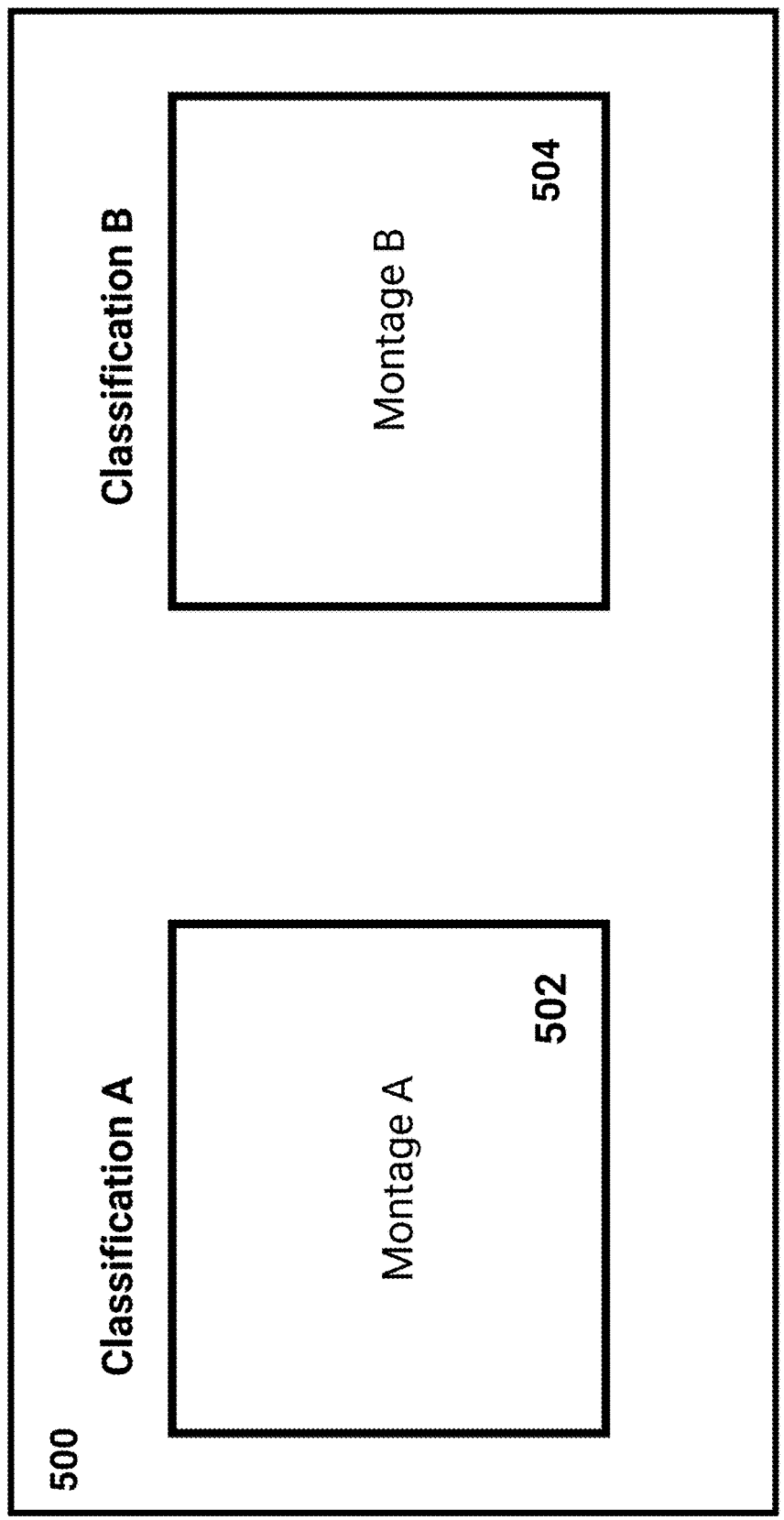
FIG. 5 illustrates an example user interface for re-classifying medical images.

FIG. 5 illustrates an example user interface 500 for re-classifying medical images. As described above, a reviewing user can utilize a user interface to review two or more montages 502, 504, each with medical images classified according to a respective classification. For example, montage A 502 may include medical images with lesions that are classified as oval. Montage B 504 may include medical images with lesions that are classified as round. As another example, montage A 502 may include medical images of a portion of a bowel with a first classification, while montage B 504 may include the same portion of the bowel with a second classification.

As will be described in more detail below, and illustrated in FIGS. 6A-6C, a reviewing user utilizing user interface 500 can cause the re-classification of particular medical images or groups of medical images. As described above, a final classification may be determined for each medical image. That is, a threshold number of reviewing users (e.g., 2, 3, 5) may be required to classify a medical image prior to a final classification being assigned. A secondary reviewing user may utilize user interface 500 to review prior classifications assigned by one or more other reviewing users. Optionally, a same reviewing user who classified medical images included in montage A 502 and montage B 504 can utilize the user interface 500 to review his/her classifications.

Figure 6A:
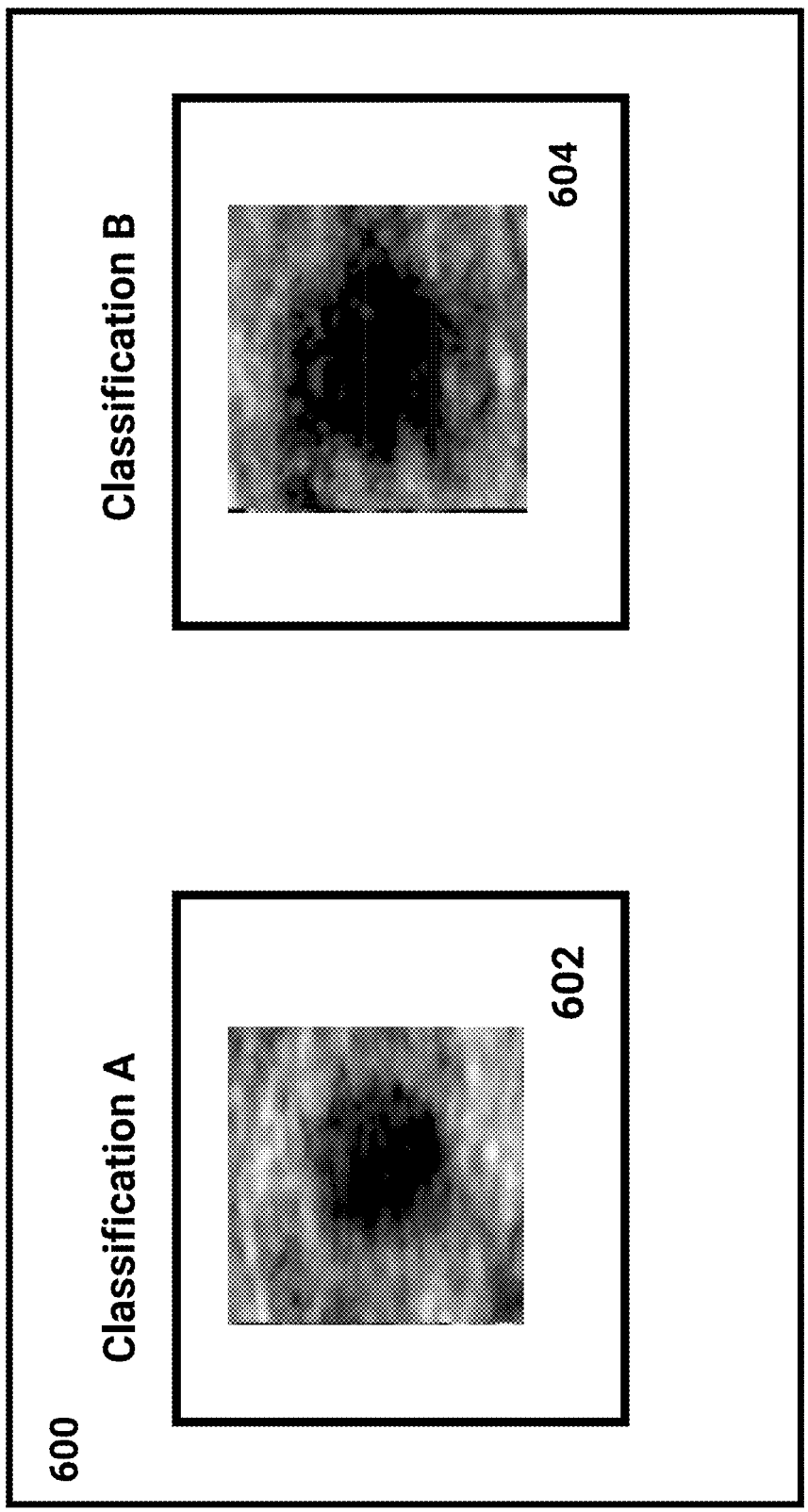
FIG. 6A illustrates an example user interface for re-classifying medical images.
Figure 6B:
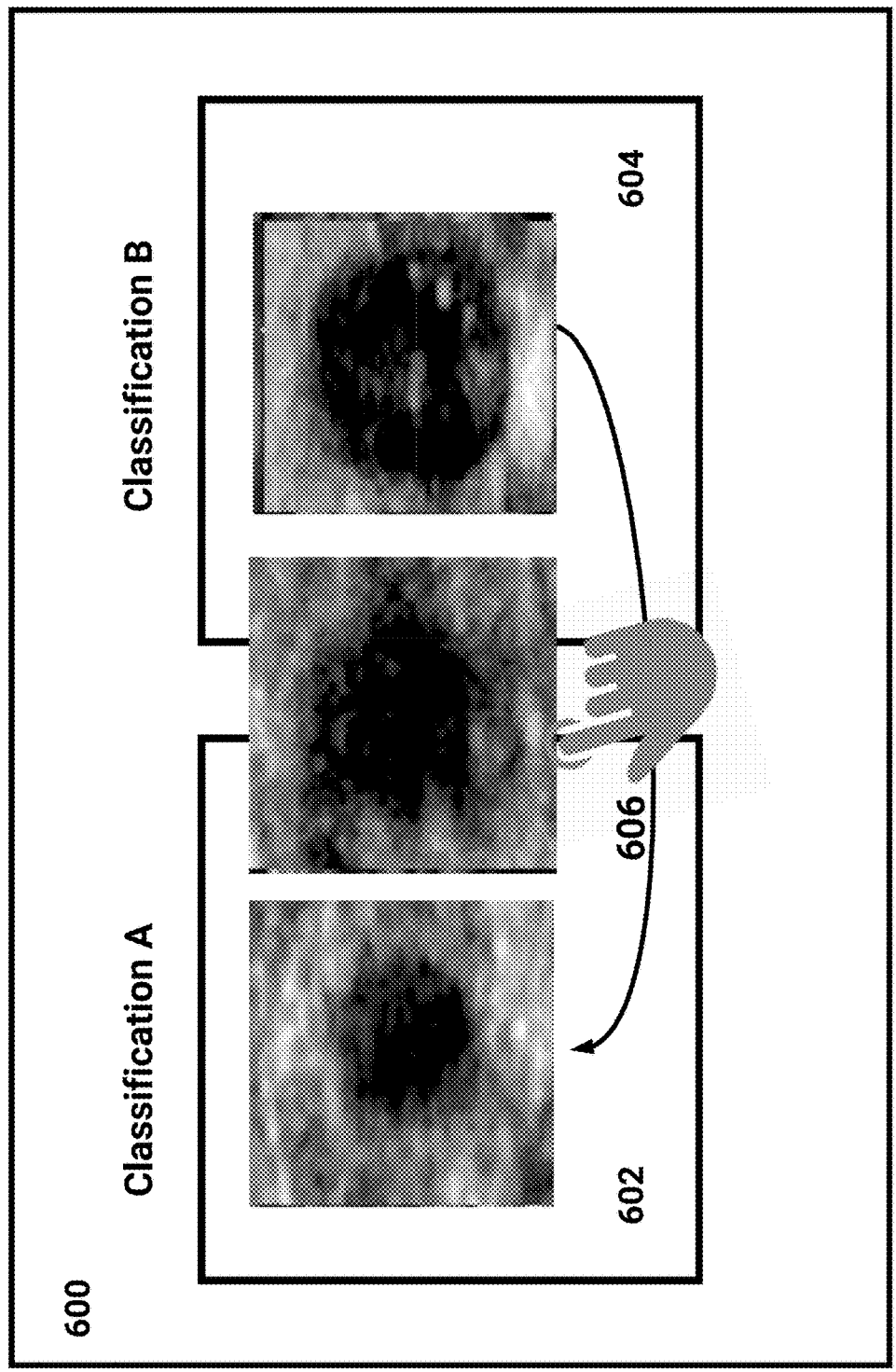
FIG. 6B illustrates an example of a user re-classifying a medical image.

While the example user interfaces of FIG. 6A-6C illustrate montages as respective stacks of medical images, montages in this re-classification embodiment may be represented as a grid (e.g. montage 302) or other non-grid organization of non-overlapping, partially overlapping, or stacked medical images. For example, if a display presenting the user interfaces described in FIGS. 6A-6C is of sufficient size (e.g., a size such that two M×N grids, as described above, can be presented at a same time on the display), the montages may be presented as respective grids.

FIG. 6A illustrates an example user interface 600 for re-classifying medical images. In the example of FIG. 6A, the medical images include objects (e.g., lesions) classified according to a shape. For example, classification A associated with montage 602 may include lesions of a first shape (e.g., round), while classification B associated with montage 604 may include lesions of a second shape (e.g., oval).

A reviewing user utilizing user interface 600 can interact with the user interface 600 to indicate that a medical image is to be re-classified. For example, FIG. 6B illustrates the reviewing user dragging medical image 606 included in montage 604 to montage 602. As illustrated, the reviewing user may utilize a touch-sensitive display to interact with user interface 600. For example, the reviewing user can press on medical image 606 for greater than a threshold amount of time (e.g., 0.5 seconds, 1 seconds), or press on the display with greater than a threshold force or pressure, to indicate that the medical image 606 is to be dragged. As another example, the reviewing user can utilize a keyboard and/or mouse to manipulate medical image 606. Optionally, the reviewing user can verbally provide commands to re-classify medical image 606 (e.g., a conversational interface).

Once the reviewing user re-classifies the medical image 606 according to classification A, the user interface 600 can update to indicate that medical image 606 is included in montage 602. For example, the user interface 600 may present an animation illustrating the medical image 606 being included in the montage 602 stack. To separate the medical image 606 from the medical images in montage 602 that are awaiting review, the medical image 606 may be included at a bottom of the montage stack 602. Additionally, if the reviewing user reviews all other medical images in montage stack 602, the user interface 600 can present information informing the reviewing user that he/she has completed review. In this way, the reviewing user can avoid reviewing medical image 606 for an additional time.

While the example of FIG. 6B illustrates the reviewing user re-classifying medical image 606, some of the medical images of the stacked montage 602, 604 may be correctly classified. In this scenario, the reviewing user can swipe the medical image in a particular direction (e.g., up, down, opposite from a montage associated with a different classification, and so on) to indicate correct classification of the image. This medical image may then disappear from further review. Optionally, a portion adjacent to each montage (e.g., underneath each montage) may be utilized by the reviewing user to place correctly classified medical images.

FIG. 6C illustrates another example user interface 600 for re-classifying medical images. As described above, FIG. 6B illustrates a reviewing user dragging a medical image 606 from a first montage 604 to a second montage 602. Once the medical image 606 is included in montage 602, the medical image 606 may optionally be included at an end of the stack montage 602. In contrast, FIG. 6C illustrates the medical image 606 being included in a portion 610 of the user interface 600 associated with re-classified medical images.

As illustrated, the user interface 600 includes a portion 610, 612, adjacent to each montage 602, 604. To re-classify medical image 606 according to Classification A, the reviewing user can drag medical image 606 onto portion 610. The portions 610, 612, may therefore include re-classified medical images. Optionally, the portions may be presented as a grid, such as described above with respect to FIGS. 3A-3C, enabling the reviewing user to view all re-classified medical images.

Figure 7:
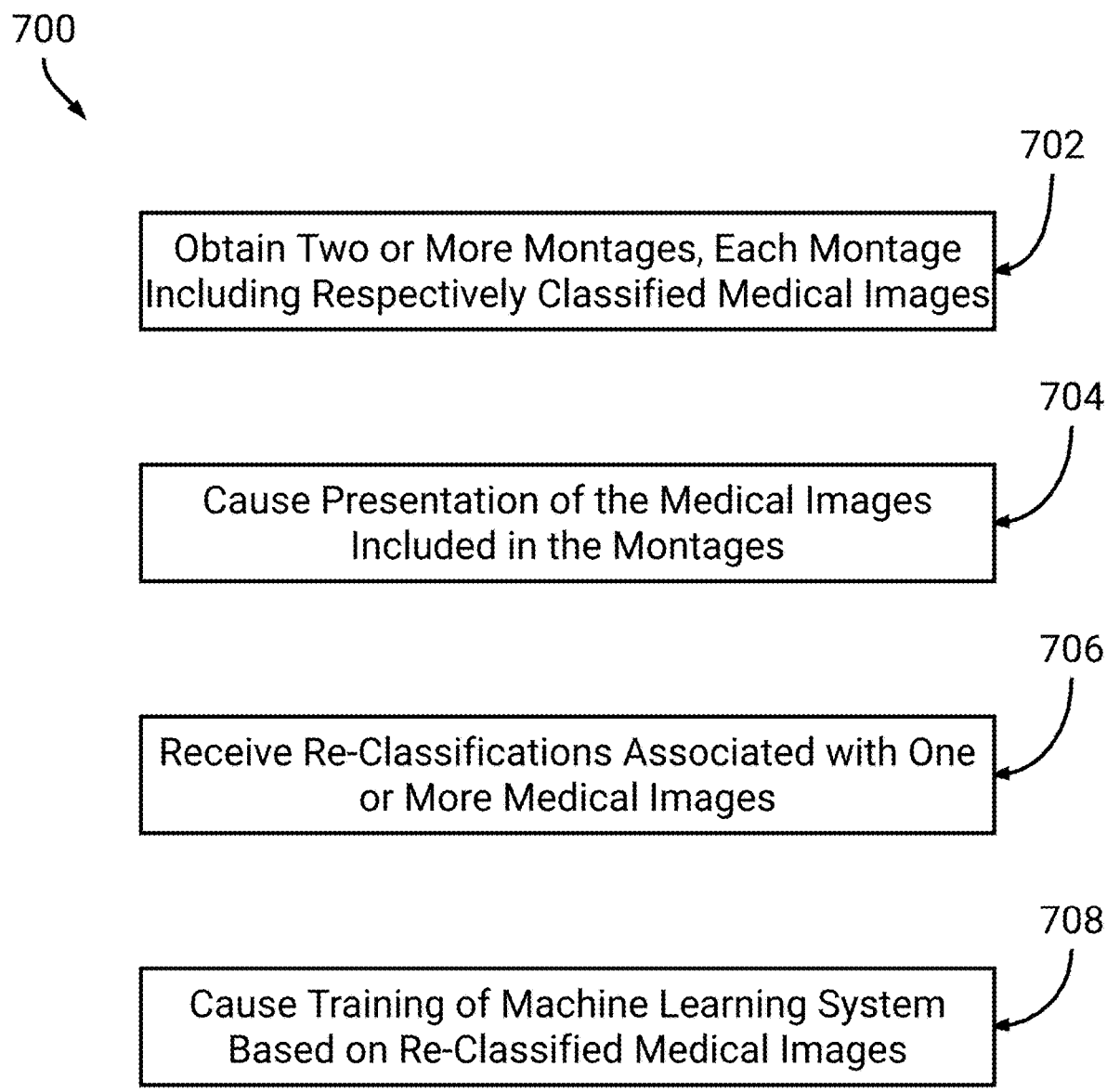
FIG. 7 illustrates an example process for re-classifying medical images.

FIG. 7 illustrates an example process 700 for re-classifying medical images. For convenience, the process 700 will be described as being performed by a system of one or more computers (e.g., the medical image classification system 100).

The system obtains two or more montages with each montage including medical images classified according to a same classification (block 702). A reviewing user may request two or more montages for secondary review, for example the montages may include medical images that have not been reviewed a threshold number of times. Additionally, the montages may include one or more medical images for which an initial reviewing user indicated that a secondary review is required.

Optionally the system may present montages automatically to the reviewing user, for example according to configurable rules. As an example, a first montage may include medical images associated with a particular risk. A second montage may include medical images associated with a different risk. These two montages may be automatically selected for presentation, enabling the reviewing user to confirm that each medical image was properly classified (e.g., according to risk). The rules may be based on the particular reviewing user (e.g., the reviewing user can indicate rules associated with presenting two or more montages). Additionally, the rules can be based on a user role of the reviewing user, for example the medical images included in the two or more montages can be include features or objects relevant to a particular practice area, or specialty, of the reviewing user. The user role can be based on an experience level, for example particular classifications may be easier to assign. For these particular classifications, one or more rules may indicate that reviewing users with less than a threshold experience level be assigned to review the two or more montages. Rules may additionally be related to patient attributes (e.g., the two or more montages may include medical images from patients with similar attributes, such as age, medical indicia, demographic information, and so on), suspected disease, and so on.

The system causes presentation of medical images included in the montages (block 704). As illustrated in FIGS. 6A-6C, for example, user interfaces can be presented to a reviewing user that enable the reviewing user to re-classify one or more of the medical images.

Optionally, control images may be included in one or more of the montages. For example, the system can access medical images having been finally classified previously (e.g., by a threshold number of users and/or by a threshold cumulative expertise level of classifying users), and group the medical images into a montage according to classification. The system can include one or more control images that are known to be classified according to the same classification as the montage. For example, a known round object may be included in a montage of classified round objects. Similar to the description above regarding control images, the control images can be utilized as a framework by the reviewing user. As an example, a control image including a known round object can be viewed by the reviewing user, and utilized to classify or re-classify medical images. The control images may further be utilized to validate credentials of the reviewing user. Additionally, if the reviewing user incorrectly classifies more than a threshold number of control images, the user interface can dynamically update to indicate that his/her re-classifications are to be discarded or will require review by another reviewing user.

The system receives re-classifications of one or more medical images (block 706). As illustrated in FIGS. 6B-6C, the reviewing user can indicate that a medical image is to be re-classified. For example, the reviewing user can drag a medical image from a first montage for inclusion in a second montage. A re-classification may optionally trigger a subsequent reviewing user's review of the re-classification. For example, since the re-classification can represent a disagreement between a first reviewing user and a second reviewing user, the system can enable a third reviewing user to classify the medical image (e.g., settle the disagreement). Additionally, if the first classification was assigned by a system (e.g., a machine learning system) or a user with a lower expertise in classifying images, the system can optionally prefer the classification by the second reviewing user and can avoid causing a third reviewing user to classify the medical image. Similarly, both the initial classification and re-classification may have been assigned by machine learning systems, and a human reviewing user may settle any disagreements between the machine learning systems. That is, the human reviewing user may utilize a user interface displaying the medical image, and assign a classification to the medical image.

For a re-classified medical image, a reviewing user who initially classified the medical image can be alerted. For example, the initial reviewing user may receive a notification on his/her user device informing the initial reviewing user of the re-classification. Optionally, the notification may include description of the new classification. The notification may further enable the initial reviewing user to contact the reviewing user who re-classified the medical image.

The re-classified medical images may be stored by the system, and optionally the re-classifications may be utilized as the classifications of the medical images. Optionally, the system may store the initial classifications along with any re-classifications. In this way, the system can track a progression of classification of the medical images. Additionally, the system may determine a final classification based on the initial classification and any re-classifications. For example, and as described above, the system can utilize performance of reviewing users with respect to control images to determine which user's classifications, and possibly relative weightings for each user's classifications, are the basis of the final classification. Optionally, the system can cause additional review of a re-classified medical image until a threshold number of reviewing users (e.g., 1, 2, 3) classify the medical image according to a same classification. This same classification can then be assigned as the final classification to the medical image.

Furthermore, optionally the initial classifications of medical images may be automatically performed by a machine learning system. For example, the machine learning system may be trained on medical images which have been classified (e.g., as described above, with respect to FIG. 4). Thereafter, the machine learning system can perform classifications of medical images and optionally a reviewing user can subsequently review the classifications utilizing the user interfaces described in FIGS. 6A-6C. As medical images are re-classified, the machine learning system can be updated based on the re-classifications. That is, the machine learning system can utilize the re-classifications to update connection weightings associated with neurons in a neural network, update a generated model, and so on.

The system causes training of a machine learning system based on the re-classified medical images (block 708). As described above, the system can cause a machine learning system to update based on the re-classifications. In this way, an initial classification process (e.g., the process described in FIG. 4) may be effectively performed by a machine learning system.

Additional Embodiments

Any process descriptions, elements, or blocks in the flow diagrams described herein and/or depicted in the attached figures should be understood as potentially representing modules, segments, or portions of code which include one or more executable instructions (as described below) for implementing specific logical functions or steps in the process. Alternate implementations are included within the scope of the embodiments described herein in which elements or functions may be deleted, executed out of order from that shown or discussed, including substantially concurrently (for example, through multi-threaded processing, interrupt processing, or multiple processors or processor cores or on other parallel architectures) or in reverse order, depending on the functionality involved.

Any of the methods and processes described above may be partially or fully embodied in, and partially or fully automated via, logic instructions, software code instructions, and/or software code modules executed by one or more general purpose processors and/or application-specific processors (also referred to as "computer devices," "computing devices," "hardware computing devices," "hardware processors," and the like). For example, the methods described herein may be performed as software instructions are executed by, and/or in response to software instruction being executed by, one or more hardware processors (e.g., one or more processors of the computing system 100) and/or any other suitable computing devices. The software instructions and/or other executable code may be read from a tangible computer-readable medium. A tangible computer-readable medium is a data storage device that can store data that is readable by a computer system and/or computing devices. Examples of computer-readable mediums include read-only memory (ROM), random-access memory (RAM), other volatile or non-volatile memory devices, DVD-ROMs, CD-ROMs, magnetic tape, flash drives, and/or optical data storage devices. Accordingly, a software module may reside in RAM memory, flash memory, ROM memory, EPROM memory, EEPROM memory, registers, hard disk, solid state drive, a removable disk, a CD-ROM, a DVD-ROM, and/or any other form of a tangible computer-readable storage medium.

Additionally, any of the methods and processes described above may be partially or fully embodied in, and partially or fully automated via, electronic hardware (for example, logic circuits, hardware processors, and/or the like). For example, the various illustrative logical blocks, methods, routines, and the like described in connection with the embodiments disclosed herein may be implemented as electronic hardware, computer software, or combinations of both. To illustrate this, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method for facilitating proper classification of features in medical images comprising:
   generating, for display on a display of a computing system, an interactive classification user interface concurrently displaying a first group of medical images and a second group of medical images, wherein each of the first group of medical images depicts an object associated with a first classification and each of the second group of medical images depicts an object associated with a second classification;
   detecting user input indicating movement of one or more medical images from the first group to the second group;
   in response to the user input, re-classifying the one or more medical images as associated with the second classification; and
   providing the re-classifications to a machine learning system.

2. The method of claim 1, wherein the first group of medical images is displayed as a grid.

3. The method of claim 1, wherein the first group of medical images is displayed as a stack.

4. The method of claim 1, wherein each medical image is associated with a user who classified the medical image, and wherein the method further comprises:

accessing information indicating users associated with the moved medical images; and generating respective notifications for presentation to the indicated users identifying the re-classification.

5. The method of claim 1, wherein, the machine learning system updates based on analysis of object characteristics of the re-classified one or more medical images to increase an accuracy associated with automated assignment of classifications.

6. A method for facilitating proper classification of features in medical images comprising:

generating, for display on a display of a computing system, an interactive classification user interface concurrently displaying two groups of medical images, each group having been assigned a disparate classification relating to objects included in the medical images, and each object having been extracted from a larger medical image;

the interactive classification user interface enabling a user to adjust a classification of each medical image to correspond to a different group, such that the medical image is re-classified according to the different classification; and providing the re-classifications to a machine learning system, the machine learning system updating based on the re-classifications to increase an accuracy associated with assigning classifications.

7. The method of claim 6, wherein borders of the objects included in the medical images are highlighted, the highlighting being automatically generated by the machine learning system.

8. The method of claim 6, wherein the interactive classification user interface displays each group of medical images as a respective grid.

9. The method of claim 6, wherein the interactive classification user interface displays each group of medical images as a respective stack.

10. The method of claim 6, wherein the interactive classification user interface receives input from the user on a touch-screen display, the input representing the user dragging a first image included in a first group to a second group, such that the first image is re-classified.

11. The method of claim 6, wherein the interactive classification user interface is configured to receive input via a touch-sensitive display, and wherein received input directed to a particular medical image causes the interactive classification user interface to update to present a full image context related to the particular medical image.

12. The method of claim 6, wherein a re-classification assigned by the user is stored, and wherein an initial user who classified the associated medical image is alerted.

13. The method of claim 6, wherein a threshold number of users assign classifications to the medical images, and wherein a final classification is determined for each medical image prior to providing the classifications to the machine learning system.

14. The method of claim 6, wherein the classifications relate to a diagnosis associated with an object, a shape of an object, or a change in size or character of an object over time.

15. Non-transitory computer storage-media storing instructions that when executed by a system of one or more computers, cause the one or more computers to perform operations comprising:

providing a visual concurrent display of two groups of medical images, each group being associated with a respective classification, wherein the classification relates to objects included in the medical images;

providing a user interface enabling a reviewing user to re-classify medical images, such that one or more medical images are assigned to a different group;

responsive to the reviewing user utilizing the user interface to indicate that a particular medical image is to be re-classified, updating the particular image to be assigned to the different group and causing storage of the update.

16. The computer storage-media of claim 15, wherein the operations further comprise:

training a machine learning system based on the re-classification.

17. The computer storage-media of claim 15, wherein each group is presented as a respective grid of medical images.

18. The computer storage-media of claim 15, wherein each group is presented as a respective stack of medical images.

19. The computer storage-media of claim 15, wherein an initial reviewing user who classified the particular medical image is alerted.

20. The computer storage-media of claim 15, wherein a notification is provided to a third reviewing user, the notification enabling activation of an application on a user device of the third reviewing user to determine a final classification for the particular medical image.

* * * * *